(12) United States Patent
Subramanian et al.

(10) Patent No.: US 12,053,295 B2
(45) Date of Patent: Aug. 6, 2024

(54) TRACKING NOCICEPTION UNDER ANESTHESIA USING A MULTIMODAL METRIC

(71) Applicant: Massachusetts Institute of Technology, Cambridge, MA (US)

(72) Inventors: Sandya Subramanian, Cambridge, MA (US); Emery Brown, Brookline, MA (US); Riccardo Barbieri, Boston, MA (US)

(73) Assignees: Massachusetts Institute of Tehnology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 18/314,473

(22) Filed: May 9, 2023

(65) Prior Publication Data

US 2023/0363702 A1      Nov. 16, 2023

Related U.S. Application Data

(63) Continuation of application No. 17/627,450, filed as application No. PCT/US2020/042031 on Jul. 15, 2020, now abandoned.
(Continued)

(51) Int. Cl.
  *A61B 5/00*      (2006.01)
  *A61B 5/0205*    (2006.01)
  (Continued)

(52) U.S. Cl.
  CPC .......... *A61B 5/4821* (2013.01); *A61B 5/0205* (2013.01); *A61B 5/0533* (2013.01);
  (Continued)

(58) Field of Classification Search
  CPC ....... A61B 5/4821; A61B 5/28; A61B 5/4839; A61B 5/02405; A61B 5/742;
  (Continued)

(56) References Cited

U.S. PATENT DOCUMENTS 6,571,124 B1   5/2003   Storm
6,807,965 B1   10/2004  Hickle
(Continued)

FOREIGN PATENT DOCUMENTS

EP   1618840 A1   1/2006
EP   1704819 A2   9/2006
(Continued)

OTHER PUBLICATIONS

S. Subramanian, R. Barbieri and E. N. Brown, "A Point Process Characterization Of Electrodermal Activity," 2018 40th Annual International Conference of the IEEE Engineering in Medicine and Biology Society (EMBC), 2018, pp. 37-40 (Year: 2018).*
(Continued)

*Primary Examiner* — Lynsey C Eiseman
*Assistant Examiner* — Amanda L Steinberg
(74) *Attorney, Agent, or Firm* — Smith Baluch LLP

(57) ABSTRACT

Systems and methods for tracking sympathetic-driven arousal state (SDAS) including nociception under anesthesia is described herein. The method includes obtaining heart rate variability and electrodermal activity of a subject. Point process models are generated for the heart rate variability and the electrodermal activity. A multimodal approach is implemented to determine a state space framework based on these point process models. SDAS can be estimated using the state space framework. In some implementations, an anesthesiologist can modify the dosage of drugs administered to the subject based on this estimation.

17 Claims, 25 Drawing Sheets

Related U.S. Application Data

(60) Provisional application No. 62/874,300, filed on Jul. 15, 2019.

(51) Int. Cl.

| | |
|---|---|
| *A61B 5/024* | (2006.01) |
| *A61B 5/0533* | (2021.01) |
| *A61B 5/28* | (2021.01) |
| *A61M 5/172* | (2006.01) |

(52) U.S. Cl.
CPC .............. *A61B 5/28* (2021.01); *A61B 5/4839* (2013.01); *A61B 5/742* (2013.01); *A61M 5/1723* (2013.01); *A61B 5/02405* (2013.01); *A61M 2202/048* (2013.01); *A61M 2205/3303* (2013.01); *A61M 2230/04* (2013.01); *A61M 2230/06* (2013.01); *A61M 2230/65* (2013.01)

(58) Field of Classification Search
CPC .............. A61B 5/0533; A61B 5/0205; A61M 2230/65; A61M 2230/06; A61M 2230/04; A61M 2205/3303; A61M 2202/048; A61M 5/1723

See application file for complete search history.

(56) References Cited

U.S. PATENT DOCUMENTS

| | | | |
|---|---|---|---|
| 6,868,345 | B1 | 3/2005 | Jensen |
| 7,236,832 | B2 | 6/2007 | Hemmerling et al. |
| 7,308,894 | B2 | 12/2007 | Hickle |
| 7,407,485 | B2 | 8/2008 | Huiku |
| 7,407,486 | B2 | 8/2008 | Huiku et al. |
| 7,635,337 | B2 | 12/2009 | Huiku et al. |
| 7,991,462 | B2 | 8/2011 | Storm |
| 8,027,717 | B2 | 9/2011 | Storm |
| 8,512,240 | B1 | 8/2013 | Zuckerman-Stark et al. |
| 9,282,934 | B2 | 3/2016 | Liley et al. |
| D760,395 | S | 6/2016 | Barbaric et al. |
| 9,833,155 | B2 | 12/2017 | Tognetti et al. |
| 10,134,378 | B1 | 11/2018 | Cenci et al. |
| 10,285,602 | B2 | 5/2019 | Tognetti et al. |
| D867,599 | S | 11/2019 | Barbaric et al. |
| 10,506,944 | B2 | 12/2019 | Tognetti et al. |
| 2004/0015091 | A1* | 1/2004 | Greenwald ........ A61B 5/02125 600/513 |
| 2006/0089559 | A1* | 4/2006 | Barbieri .............. A61B 5/318 600/509 |
| 2006/0135879 | A1 | 6/2006 | Liley |
| 2006/0217628 | A1 | 9/2006 | Huiku |
| 2007/0010756 | A1 | 1/2007 | Viertio-Oja |
| 2010/0056943 | A1 | 3/2010 | Storm |
| 2010/0076273 | A1 | 3/2010 | Shigetou |
| 2010/0249638 | A1 | 9/2010 | Liley |
| 2011/0086922 | A1 | 4/2011 | Kohane et al. |
| 2011/0137134 | A1 | 6/2011 | Hemmerling et al. |
| 2011/0144523 | A1 | 6/2011 | Storm |
| 2011/0307079 | A1 | 12/2011 | Oweiss et al. |
| 2012/0191425 | A1 | 7/2012 | Mott et al. |
| 2013/0018249 | A1 | 1/2013 | Storm |
| 2013/0245486 | A1 | 9/2013 | Simon et al. |
| 2014/0316229 | A1 | 10/2014 | Tognetti et al. |
| 2015/0080754 | A1 | 3/2015 | Purdon et al. |
| 2015/0327787 | A1 | 11/2015 | Tognetti et al. |
| 2016/0213314 | A1 | 7/2016 | Zuckerman-Stark et al. |
| 2017/0135631 | A1* | 5/2017 | Zuckerman-Stark ........................ A61B 5/318 |
| 2017/0172443 | A1 | 6/2017 | Logier et al. |
| 2018/0206776 | A1 | 7/2018 | Nogueira et al. |
| 2018/0206784 | A1 | 7/2018 | Jensen et al. |
| 2018/0214040 | A1 | 8/2018 | Tognetti et al. |
| 2019/0022397 | A1* | 1/2019 | Srivastava ........ A61N 1/36139 |
| 2019/0259368 | A1 | 8/2019 | Cenci et al. |
| 2022/0323002 | A1 | 10/2022 | Subramanian et al. |

FOREIGN PATENT DOCUMENTS

| | | |
|---|---|---|
| EP | 1704818 A3 | 11/2006 |
| EP | 1642525 B1 | 3/2010 |
| EP | 1858409 B1 | 4/2012 |
| EP | 2967415 A1 | 1/2016 |
| EP | 3110321 A1 | 1/2017 |
| EP | 2948043 | 3/2017 |
| JP | 2019048128 A | 3/2019 |
| JP | 2019177175 A | 10/2019 |
| WO | 2002071550 A1 | 9/2002 |
| WO | 2003075760 A1 | 9/2003 |
| WO | 2003094726 A1 | 11/2003 |
| WO | 2004052048 A1 | 6/2004 |
| WO | 2004054441 A1 | 7/2004 |
| WO | 2005051201 A1 | 6/2005 |
| WO | 2005117699 A1 | 12/2005 |
| WO | 2007097634 A1 | 8/2007 |
| WO | 2007140535 A1 | 12/2007 |
| WO | 2007140536 A1 | 12/2007 |
| WO | 2008043365 | 11/2008 |
| WO | 2009063463 A2 | 5/2009 |
| WO | 2009112570 A1 | 9/2009 |
| WO | 2010043054 A1 | 4/2010 |
| WO | 2010047599 A1 | 4/2010 |
| WO | 2014115075 A1 | 7/2014 |
| WO | 2014147024 A1 | 9/2014 |
| WO | 2015128567 A1 | 9/2015 |
| WO | 2016110847 A1 | 7/2016 |
| WO | 2016146536 A1 | 9/2016 |
| WO | 2017006313 A2 | 1/2017 |

OTHER PUBLICATIONS

D. S. Wickramasuriya, C. Qi and R. T. Faghih, "A State-Space Approach for Detecting Stress from Electrodermal Activity," 2018 40th Annual International Conference of the IEEE Engineering in Medicine and Biology Society (EMBC), 2018, pp. 3562-3567 (Year: 2018).*

S. Ghiasi et al., "A New Sympathovagal Balance Index from Electrodermal Activity and Instantaneous Vagal Dynamics: A Preliminary Cold Pressor Study," 2018 40th Annual International Conference of the IEEE Engineering in Medicine and Biology Society (EMBC), 2018, pp. 3068-3071 (Year: 2018).*

Moltner et al. "Heart rate changes as an autonomic component of the pain response." Pain 43.1 (1990): 81-89.

Ogawa et al. "Characteristics of subthreshold sudomotor neural impulses." Journal of Applied Physiology 33.3 (1972): 300-305.

Ogawa et al. "Different effects on circulatory control during volatile induction and maintenance of anesthesia and total intravenous anesthesia: autonomic nervous activity and arterial cardiac baroreflex function evaluated by blood pressure and heart rate variability analysis." Journal of Clinical Anesthesia 18.2 (2006): 87-95.

Paloheimo et al. "Autonomic nervous system state: the effect of general anaesthesia and bilateral tonsillectomy after unilateral infiltration of lidocaine." British Journal of Anaesthesia 104.5 (2010): 587-595.

Posada-Quintero et al. "Highly sensitive index of sympathetic activity based on time-frequency spectral analysis of electrodermal activity." American Journal of Physiology-Regulatory, Integrative and Comparative Physiology 311.3 (2016): R582-R591.

Posada-Quintero et al. "Innovations in electrodermal activity data collection and signal processing: A systematic review." Sensors 20.2 (2020): 18 pages.

Posada-Quintero et al. "Power spectral density analysis of electrodermal activity for sympathetic function assessment." Annals of Biomedical Engineering 44.10 (2016): 3124-3135.

Posada-Quintero et al. "Time-varying analysis of electrodermal activity during exercise." PloS one 13.6 (2018): e0198328, 12 pages.

Prichep et al. "The Patient State Index as an indicator of the level of hypnosis under general anaesthesia." British Journal of Anaesthesia 92.3 (2004): 393-399.

(56) References Cited

OTHER PUBLICATIONS

Rantanen et al. "Novel multiparameter approach for measurement of nociception at skin incision during general anaesthesia." British Journal of Anaesthesia 96.3 (2006): 367-376.

Rhudy et al. "Psychophysiological responses to pain: further validation of the nociceptive flexion reflex (NFR) as a measure of nociception using multilevel modeling." Psychophysiology 46.5 (2009): 939-948.

Sano et al. "Quantitative analysis of wrist electrodermal activity during sleep." International Journal of Psychophysiology 94.3 (2014): 382-389.

Sonner et al. "The microfluidics of the eccrine sweat gland, including biomarker partitioning, transport, and biosensing implications." Biomicrofluidics 9.3 (2015): 031301 20 pages.

Storm "Changes in skin conductance as a tool to monitor nociceptive stimulation and pain." Current Opinion in Anesthesiology 21.6 (2008): 796-804.

Storm et al. "Palmar skin conductance compared to a developed stress score and to noxious and awakening stimuli on patients in anaesthesia." Acta Anaesthesiologica Scandinavica 49.6 (2005): 798-803.

Storm et al. "Skin conductance correlates with perioperative stress." Acta Anaesthesiologica Scandinavica 46.7 (2002): 887-895.

Subramanian et al. "A Model-Based Approach for Pulse Selection from Electrodermal Activity." IEEE Transactions on Bio-medical Engineering (2021), 28 pages.

Subramanian et al. "A point process characterization of electrodermal activity." 2018 40th Annual International Conference of the IEEE Engineering in Medicine and Biology Society (EMBC). IEEE, 2018, 4 pages.

Subramanian et al. "Elementary integrate-and-fire process underlies pulse amplitudes in Electrodermal activity." PLoS Computational Biology 17.7 (2021): e1009099, 17 pages.

Subramanian et al. "Multimodal vs Unimodal Estimation of Sympathetic-Driven Arousal States." 2020 Computing in Cardiology. IEEE, 2020 4 pages.

Subramanian et al. "Point process temporal structure characterizes electrodermal activity." Proceedings of the National Academy of Sciences 117.42 (2020): 26422-26428.

Subramanian et al. "Quantitative assessment of the relationship between behavioral and autonomic dynamics during propofol-induced unconsciousness." Plos one 16.8 (2021): e0254053, 15 pages.

Treister et al. "Differentiating between heat pain intensities: the combined effect of multiple autonomic parameters." PAIN® 153.9 (2012): 1807-1814.

Uncini et al. "The sympathetic skin response: normal values, elucidation of afferent components and application limits." Journal of the Neurological Sciences 87.2-3 (1988): 299-306.

Upton et al., "Intraoperative "Analgesia Nociception Index"—guided fentanyl administration during sevoflurane anesthesia in lumbar discectomy and laminectomy: a randomized clinical trial." Anesthesia & Analgesia 125.1 (2017): 81-90.

Wallin "Sympathetic nerve activity underlying electrodermal and cardiovascular reactions in man." Psychophysiology 18.4 (1981): 470-476.

Wallin et al. "Peripheral sympathetic neural activity in conscious humans." Annual Review of Physiology 50.1 (1988): 565-576.

Wallin et al. "Sympathetic neural control of integrated cardiovascular function: insights from measurement of human sympathetic nerve activity." Muscle & Nerve 36.5 (2007): 595-614.

Wickramasuriya et al. "A marked point process filtering approach for tracking sympathetic arousal from skin conductance." IEEE Access 8 (2020): 68499-68513.

Wickramasuriya et al. "A mixed filter algorithm for sympathetic arousal tracking from skin conductance and heart rate measurements in Pavlovian fear conditioning." PloS one 15.4 (2020): e0231659, 34 pages.

Wickramasuriya et al. "A state-space approach for detecting stress from electrodermal activity." 2018 40th Annual International Conference of the IEEE Engineering in Medicine and Biology Society (EMBC). IEEE, 2018, pp. 3562-3567.

Alexander et al. "Separating individual skin conductance responses in a short interstimulus-interval paradigm." Journal of Neuroscience Methods 146.1 (2005): 116-123.

Amin et al. "Sparse deconvolution of electrodermal activity via continuous-time system identification." IEEE Transactions on Biomedical Engineering 66.9 (2019): 2585-2595.

Bari "Psychological correlates of nonspecific electrodermal responses." Journal of Electrical Bioimpedance 10.1 (2019): 65-72.

Bari et al. "Electrodermal activity responses for quantitative assessment of felt pain." Journal of Electrical Bioimpedance 9.1 (2018): 52-58.

Bari et al. "Electrodermal responses to discrete stimuli measured by skin conductance, skin potential, and skin susceptance." Skin Research and Technology 24.1 (2018): 108-116.

Benedek et al. "A continuous measure of phasic electrodermal activity." Journal of Neuroscience Methods 190.1 (2010): 80-91.

Benedek et al. "Decomposition of skin conductance data by means of nonnegative deconvolution." Psychophysiology 47.4 (2010): 647-658.

Ben-Israel et al. "Monitoring the nociception level: a multi-parameter approach." Journal of Clinical Monitoring and Computing 27.6 (2013): 659-668.

Bergmann et al. "Surgical pleth index-guided remifentanil administration reduces remifentanil and propofol consumption and shortens recovery times in outpatient anaesthesia." British Journal of Anaesthesia 110.4 (2013): 622-628.

Bonhomme et al. "Comparison of the Surgical Pleth Index™ with haemodynamic variables to assess nociception—anti-nociception balance during general anaesthesia." British Journal of Anaesthesia 106.1 (2011): 101-111.

Brown et al. "Multimodal General Anesthesia in Practice." Anesthesiology News Special Edition. 2019, 11 pages.

Dahan, Nociception Monitoring Found to Improve Analgesia and Hemodynamic Stability. Anesthesiology News Jun. 11, 2019. Accessed at https://www.anesthesiologynews.com/Article/PrintArticle?articleID=55140, 4 pages.

Drover et al. "Patient state index." Best Practice & Research Clinical Anaesthesiology 20.1 (2006): 121-128.

Eriksson et al. "Skin conductance compared to a combined behavioural and physiological pain measure in newborn infants." Acta Paediatrica 97.1 (2008): 27-30.

Faghih et al. "Characterization of fear conditioning and fear extinction by analysis of electrodermal activity." 2015 37th Annual International Conference of the IEEE Engineering in Medicine and Biology Society (EMBC). IEEE, 2015 pp. 7814-7818.

Ghiasi et al. "A new sympathovagal balance index from electrodermal activity and instantaneous vagal dynamics: a preliminary cold pressor study." 2018 40th Annual International Conference of the IEEE Engineering in Medicine and Biology Society (EMBC). IEEE, 2018, pp. 3068-3071.

Ghiasi et al. "Assessing autonomic function from electrodermal activity and heart rate variability during cold-pressor test and emotional challenge." Scientific Reports 10.1 (2020): 13 pages.

Gjerstad et al. "Skin conductance or entropy for detection of non-noxious stimulation during different clinical levels of sedation." Acta Anaesthesiologica Scandinavica 51.1 (2007): 1-7.

Goddard "A pilot study of the changes of skin electrical conductance in patients undergoing general anaesthesia and surgery." Anaesthesia 37.4 (1982): 408-415.

Greco et al. "cvxEDA: A convex optimization approach to electrodermal activity processing." IEEE Transactions on Biomedical Engineering 63.4 (2015): 797-804.

Gruenewald et al. "Influence of different remifentanil concentrations on the performance of the surgical stress index to detect a standardized painful stimulus during sevoflurane anaesthesia." British Journal of Anaesthesia 103.4 (2009): 586-593.

Gruenewald et al. "Influence of nociceptive stimulation on analgesia nociception index (ANI) during propofol—remifentanil anaesthesia." British Journal of Anaesthesia 110.6 (2013): 1024-1030.

(56) References Cited

OTHER PUBLICATIONS

Gruenewald et al. "M-Entropy guidance vs standard practice during propofol-remifentanil anaesthesia: a randomised controlled trial." Anaesthesia 62.12 (2007): 1224-1229.
Gruenewald et al. "Monitoring the nociception—anti-nociception balance." Best Practice & Research Clinical Anaesthesiology 27.2 (2013): 235-247.
Hagbarth et al. "General characteristics of sympathetic activity in human skin nerves." Acta Physiologica Scandinavica 84.2 (1972): 164-176.
Hallin et al. "Afferent and efferent C units recorded from human skin nerves in situ. A preliminary report." Acta Societatis Medicorum Upsaliensis 75.5-6 (1970): 277-281.
Hallin et al. "Single unit sympathetic activity in human skin nerves during rest and various manoeuvres." Acta Physiologica Scandinavica 92.3 (1974): 303-317.
Harrison et al. "Skin conductance as a measure of pain and stress in hospitalised infants." Early Human Development 82.9 (2006): 603-608.
Hernando-Gallego et al. "Feature extraction of galvanic skin responses by nonnegative sparse deconvolution." IEEE Journal of Biomedical and Health Informatics 22.5 (2017): 1385-1394.
Huiku et al. Assessment of surgical stress during general anaesthesia. Br. J. Anaesth., 98(4):447-455, Apr. 2007.
Ilies et al. "Evaluation of the surgical stress index during spinal and general anaesthesia." British Journal of Anaesthesia 105.4 (2010): 533-537.
International Search Report and Written Opinion in International Patent Application No. PCT/US2020/042031 mailed Nov. 23, 2020, 15 pages.
Iyengar et al. "Modeling neural activity using the generalized inverse Gaussian distribution." Biological Cybernetics 77.4 (1997): 289-295.
Jain et al. "A compressed sensing based decomposition of electrodermal activity signals." IEEE Transactions on Biomedical Engineering 64.9 (2016): 2142-2151.
Jeanne et al. "Validation of a graphic measurement of heart rate variability to assess analgesia/nociception balance during general anesthesia." Conf Proc IEEE Eng Med Biol Soc. vol. 2009. 2009 p. 1840-1843.
Jeanne et al. "Variations of the analgesia nociception index during general anaesthesia for laparoscopic abdominal surgery." Journal of Clinical Monitoring and Computing 26.4 (2012): 289-294.
Kirno et al. "Can galvanic skin response be used as a quantitative estimate of sympathetic nerve activity in regional anesthesia?. " Anesthesia and Analgesia 73.2 (1991): 138-142.
Kunimoto et al. "Neuroeffector characteristics of sweat glands in the human hand activated by regular neural stimuli." The Journal of Physiology 442.1 (1991): 391-411.
Kunimoto et al. "Non-linearity of skin resistance response to intraneural electrical stimulation of sudomotor nerves." Acta Physiologica Scandinavica 146.3 (1992): 385-392.
Latson et al. "Effects of surgical stimulation on autonomic reflex function: assessment by changes in heart rate variability." BJA: British Journal of Anaesthesia 70.3 (1993): 301-305.
Ledowski et al. "Analgesia nociception index: evaluation as a new parameter for acute postoperative pain." British Journal of Anaesthesia 111.4 (2013): 627-629.
Ledowski et al. "Monitoring of sympathetic tone to assess postoperative pain: skin conductance vs surgical stress index." Anaesthesia 64.7 (2009): 727-731.
Ledowski et al. "Neuroendocrine stress response and heart rate variability: a comparison of total intravenous versus balanced anesthesia." Anesthesia & Analgesia 101.6 (2005): 1700-1705.
Ledowski et al. "New parameters of skin conductance compared with bispectral index® monitoring to assess emergence from total intravenous anaesthesia." British Journal of Anaesthesia 99.4 (2007): 547-551.
Ledowski et al. "Skin conductance monitoring compared with bispectral index® monitoring to assess emergence from general anaesthesia using sevoflurane and remifentanil." BJA: British Journal of Anaesthesia 97.2 (2006): 187-191.
Ledowski et al. "The assessment of postoperative pain by monitoring skin conductance: results of a prospective study." Anaesthesia 62.10 (2007): 989-993.
Lim et al. "Decomposing skin conductance into tonic and phasic components." International Journal of Psychophysiology 25.2 (1997): 97-109.
Logier et al. "Pain/analgesia evaluation using heart rate variability analysis." 2006 International Conference of the IEEE Engineering in Medicine and Biology Society. IEEE, 2006, pp. 4303-4306.
Martini et al. "Ability of the Nociception Level, a Multiparameter Composite of Autonomic Signals, to Detect Noxious Stimuli during Propofol—Remifentanil Anesthesia." Anesthesiology: The Journal of the American Society of Anesthesiologists 123.3 (2015): 524-534.
Mazzeo et al. "Heart rate variability: a diagnostic and prognostic tool in anesthesia and intensive care." Acta Anaesthesiologica Scandinavica 55.7 (2011): 797-811.

\* cited by examiner

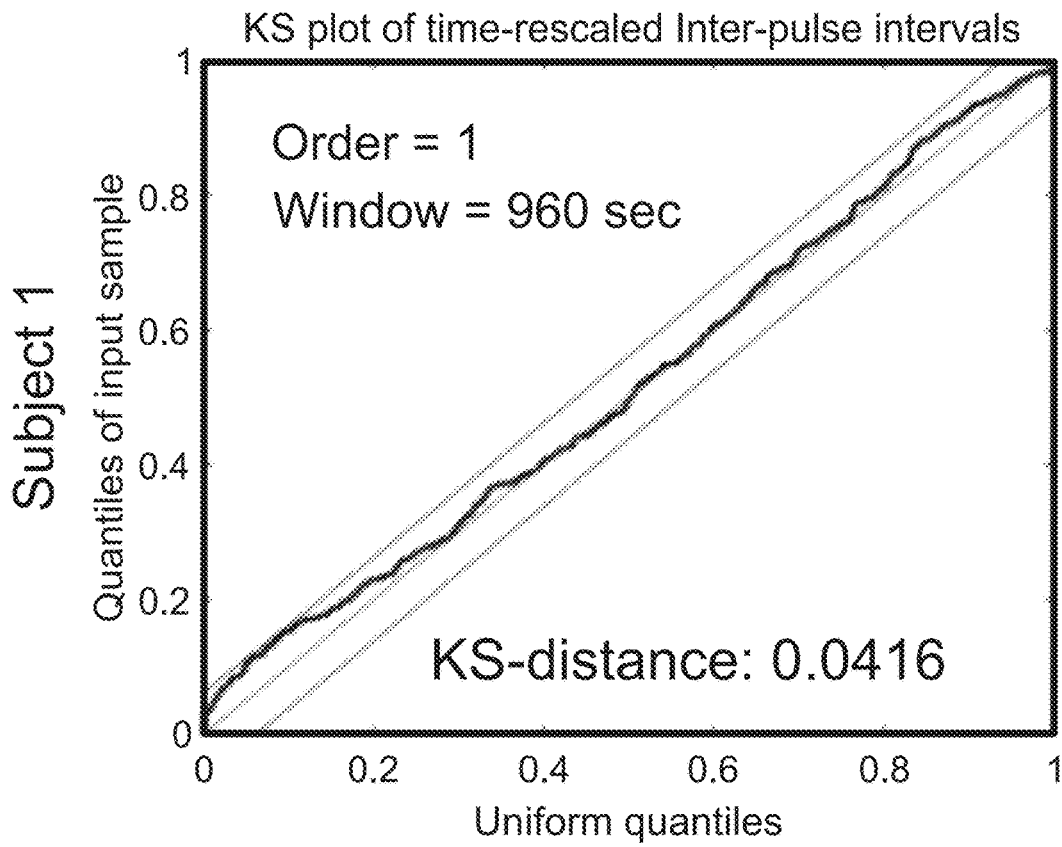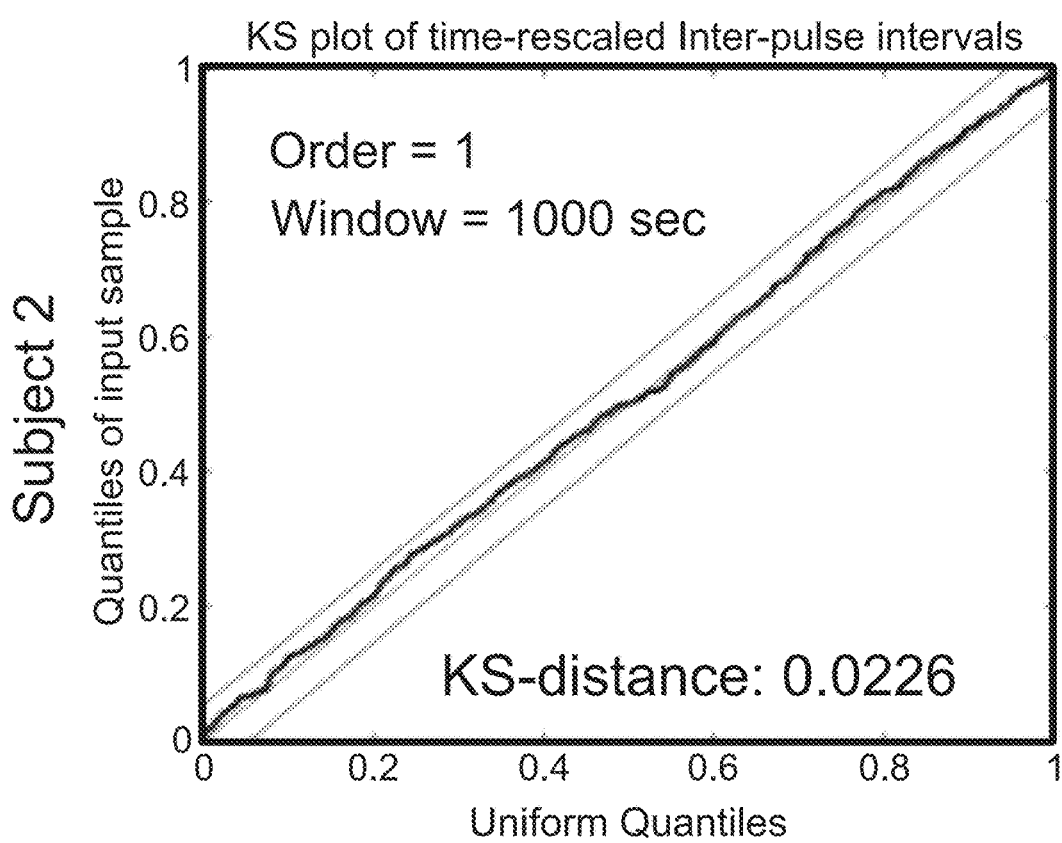
FIG. 8A

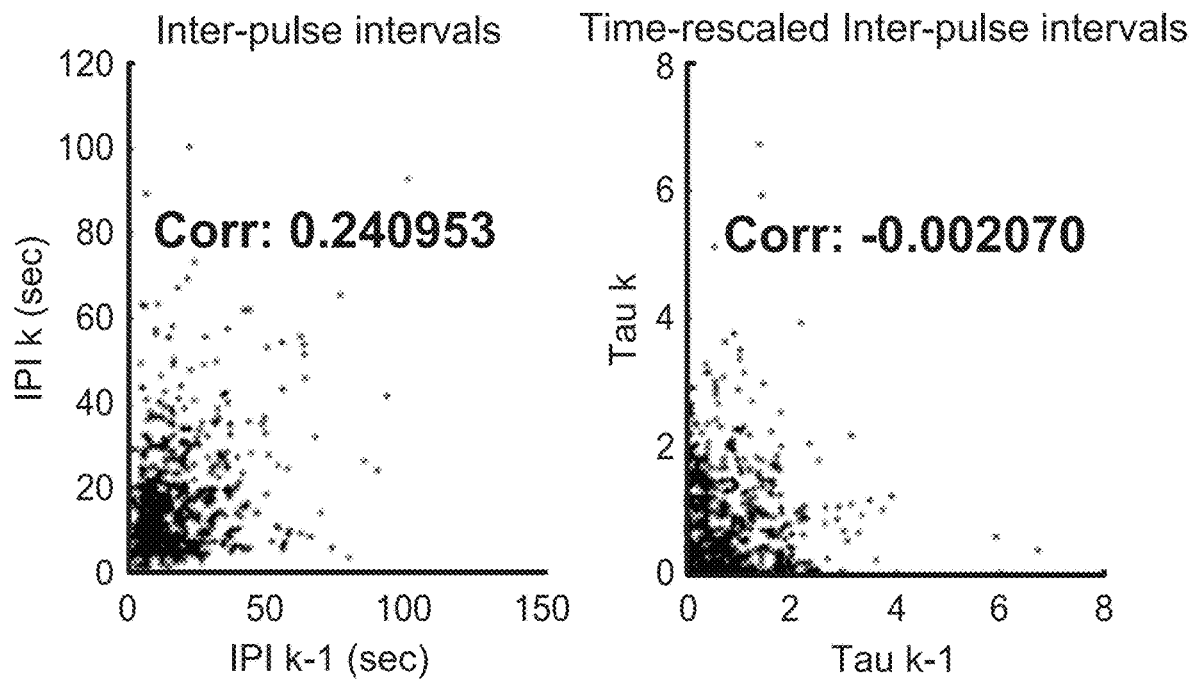
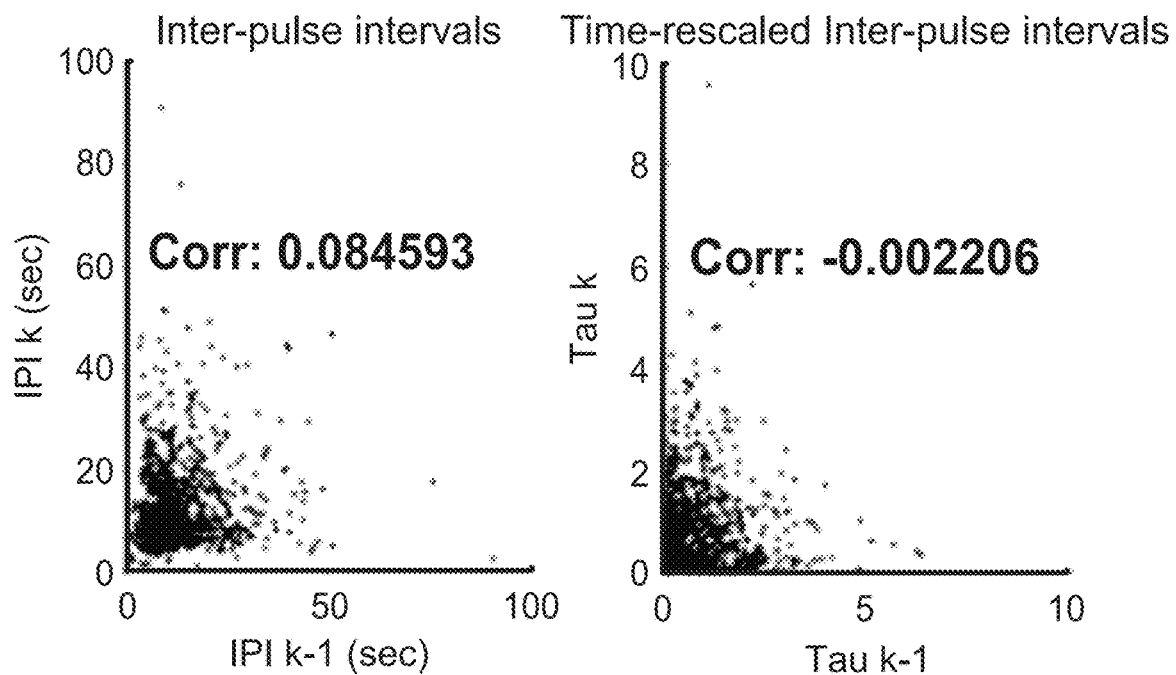
*FIG. 8B*

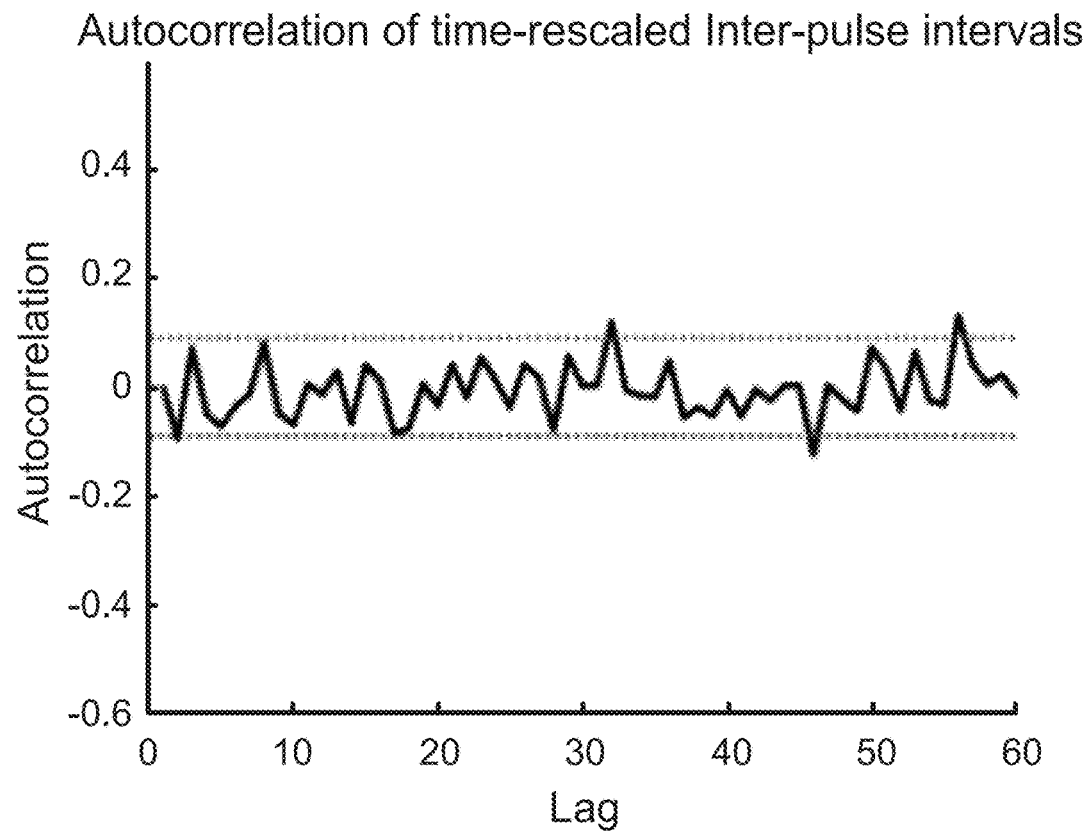
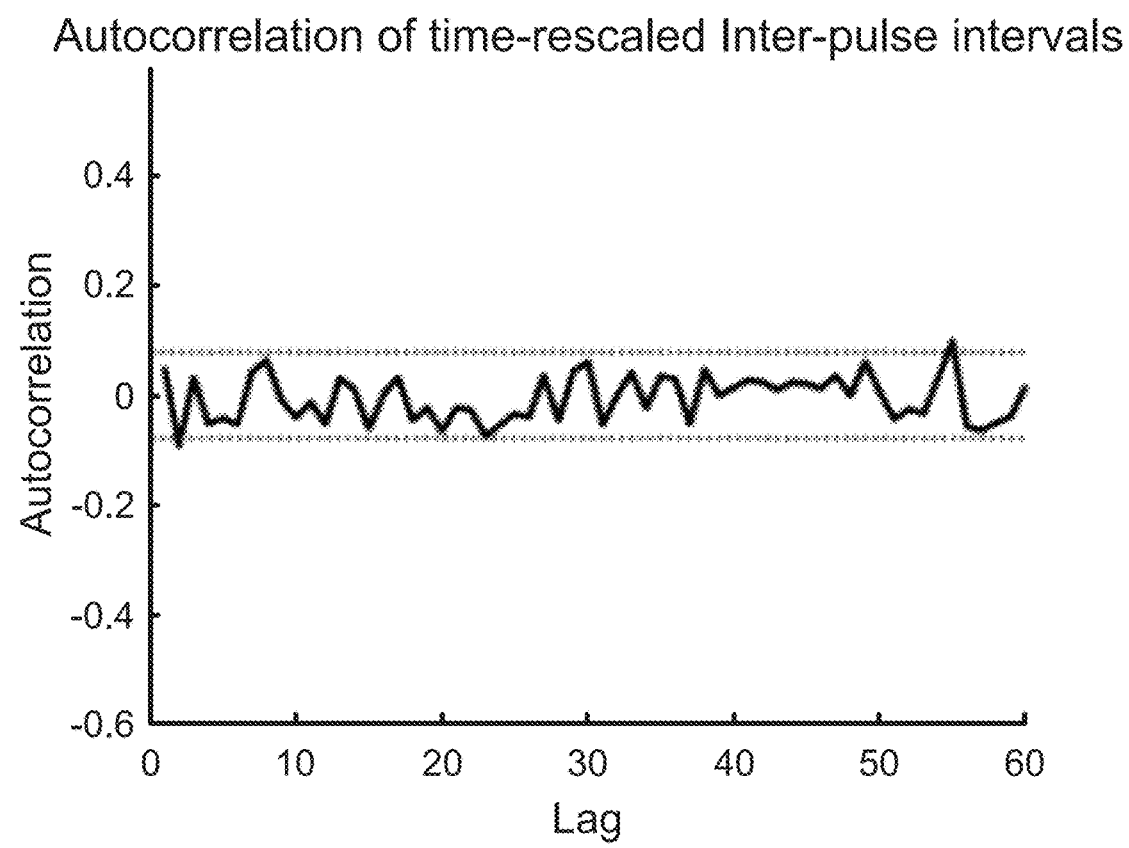
FIG. 8C

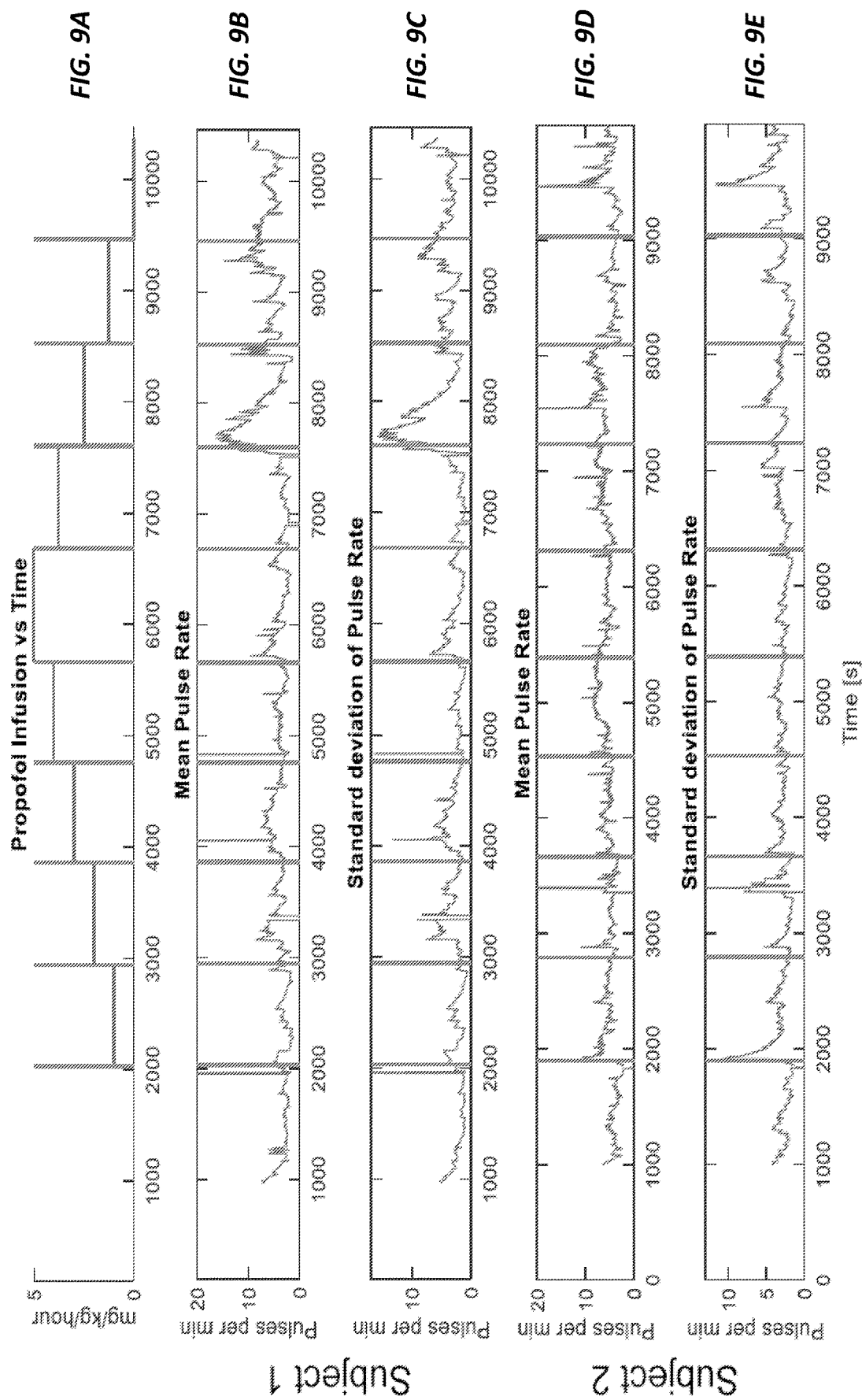

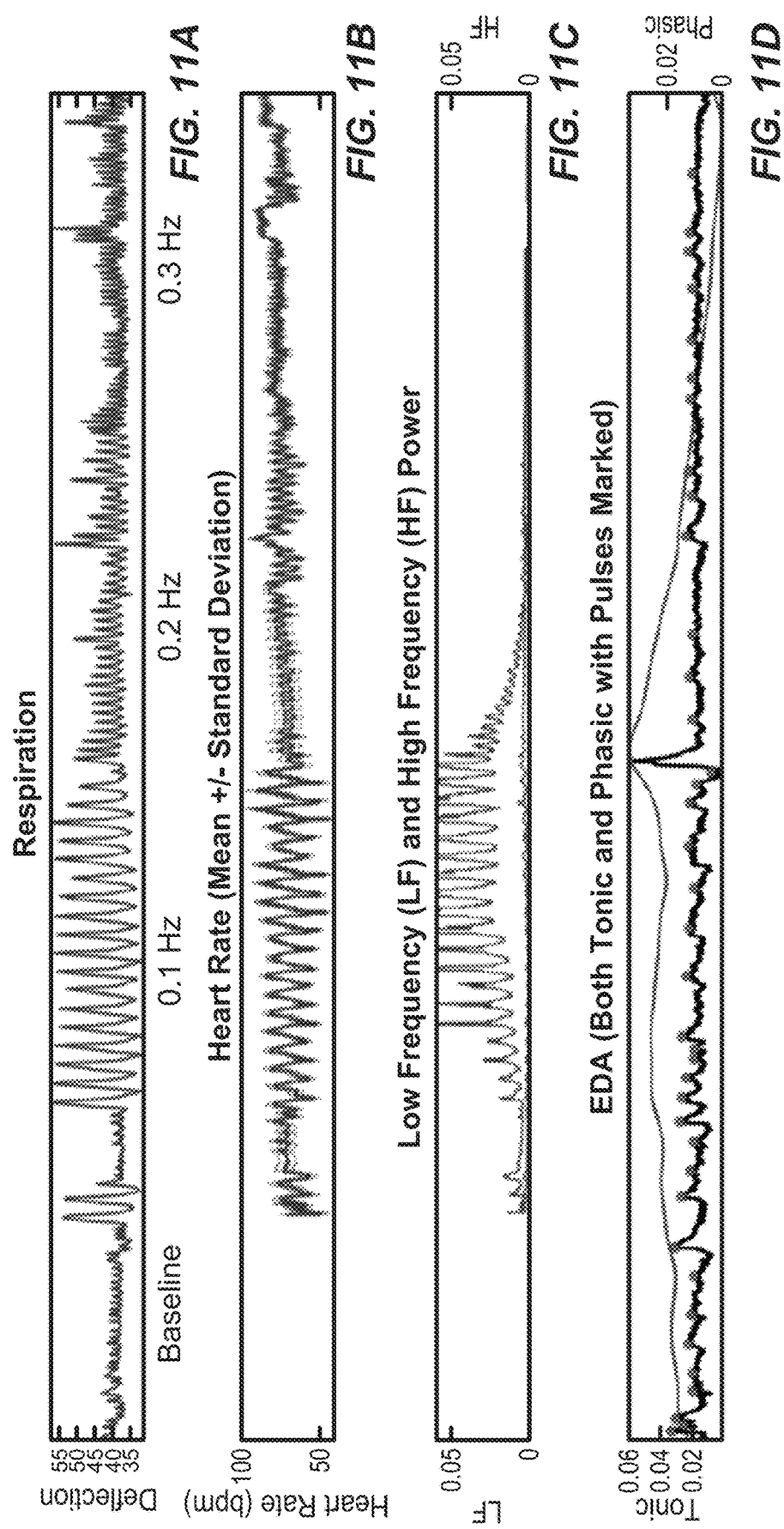

TRACKING NOCICEPTION UNDER ANESTHESIA USING A MULTIMODAL METRIC

CROSS-REFERENCE TO RELATED APPLICATIONS

This application is a continuation of U.S. application Ser. No. 17/627,450, entitled "Tracking Nociception under Anesthesia Using a Multimodal Metric," filed on Jan. 14, 2022, which is a U.S. National Stage filing under 35 U.S.C. 371 of International Application No. PCT/US2020/042031, entitled "Tracking Nociception under Anesthesia Using a Multimodal Metric," filed on Jul. 15, 2020, which claims the priority benefit, under 35 U.S.C. 119(e), of U.S. Application No. 62/874,300, entitled "A Multimodal Metric for Tracking Nociception Under Anesthesia," filed on Jul. 15, 2019, the disclosure of which is incorporated herein by reference in its entirety.

BACKGROUND

Estimating a person's sympathetic-driven arousal state (SDAS) can be challenging, especially when the person is unconscious. (A person's SDAS includes anything that drives up sympathetic activation, which in the case of surgery, is primarily nociception and some drugs that are given to maintain blood pressure.) In surgery, for example, estimating a person's nociceptive state, which is the sympathetic-driven perception of a painful or injurious stimulus, is both challenging and necessary for managing a patient's pain during surgery. Poor pain management in hospital operating and recovery rooms is a contributing factor to the opioid crisis and stems from the inability to precisely quantify nociception under anesthesia.

Nociception during surgery begins with an insult, such as a surgical incision, that activates nociceptors in the skin or viscera. The nociceptors transmit signals to the spinal cord through first-order A-δ and C-fibers. The first-order nociceptors, which have their cell bodies in the dorsal root ganglia, synapse on second-order afferents in the spinal cord and ascend in the anterolateral fasciculus to the thalamus, somatosensory cortex, association areas, prefrontal cortex, and limbic areas. These pathways make up the ascending nociceptive pathways. There are also several descending pathways for nociceptive regulation, both inhibitory and facilitatory, modulated by areas of cortex, deep brain structures, limbic areas, and areas of the brainstem, including the periaqueductal gray of the midbrain (PAG), parabrachial nuclei, dorsal raphe, and rostral ventromedial medulla (RVM). Descending projections from the RVM travel to the dorsal root where they modulate (inhibit and facilitate) the nociceptive response.

Many of these areas have a high densities of opioid receptors. The fundamental component of the nociceptive pathway that produces the autonomic response and is therefore relevant to anesthesia care is the nociceptive-medullary-autonomic (NMA) circuit. It is comprised of the spinoreticular tract, the brainstem arousal circuits, and the sympathetic and parasympathetic efferent pathways. Ascending sensory information carried by the second-order projection neurons synapse in the nucleus of the solitary tract (NTS) in the medulla and then also on the parabrachial nucleus (PBN). The autonomic response to a nociceptive stimulus is initiated from the NTS, which mediates sympathetic output to the rostral and caudal ventral lateral medulla which project to the thoracolumbar sympathetic ganglia. Projections from these ganglia carry sympathetic stimulation to the heart, blood vessels and skin. The NTS mediates parasympathetic output through the nucleus ambiguus (NA), which projects through the vagus nerve to the blood vessels and sino-atrial node of the heart. Hence, a nociceptive surgical stimulus initiates an increase in sympathetic output and a decrease in parasympathetic output through the NMA circuit, which is manifested as an increase in heart rate, an increase in blood pressure, and an increase in electrodermal activity (EDA).

Nociception can be treated by reducing transmission in nociceptive pathways, decreasing arousal and perception of nociceptive stimuli, or both simultaneously. Nociception is treated primarily by administering opioids that act on endogenous opioid receptors found throughout the central nervous system, and specifically in regions such as the PAG, RVM, and the spinal cord to enhance descending inhibitory pathways for pain. In addition, to their potency as antinociceptive agents, opioids cause side effects such as bradycardia, respiratory depression, constipation, and nausea.

Alpha-2 agonists, such as dexmedetomidine, are used for both hypnotic and analgesic effects. Dexmedetomidine inhibits noradrenergic neurons in the locus ceruleus and spinal cord leading to decreased arousal and modulation of nociception. While it has minimal effects on respiration, dexmedetomidine does decrease both blood pressure and heart rate. Non-Steroidal Anti-Inflammatory Drugs (NSAIDs) and adjunct agents such as dexmedetomidine and lidocaine act directly on nociceptive targets. Hypnotic agents such as propofol and the inhaled ethers modulate nociceptive perception by rendering a patient unconscious.

The principal anti-nociceptive effects of ketamine are due to its targeting of N-methyl-D-aspartate (NMDA) receptors located on peripheral afferent nociceptive neurons that synapse in the dorsal horn of the spinal cord. Ketamine's actions at NMDA receptors in the cortex and other parts of the arousal system contribute both to its anti-nociceptive effects and to its capacity to decrease arousal. At low doses, ketamine binds preferentially to NMDA receptors on GABAergic inhibitory interneurons leading to general disinhibition of pyramidal neurons and diffuse excitatory cortical activity. This activity is marked by gamma oscillations (25-30 Hz) in the electroencephalogram and an altered state of arousal that commonly includes hallucinations. At higher doses, ketamine also blocks NMDA receptors on excitatory pyramidal neurons. Key targets for altering arousal are the glutamatergic projections from the parabrachial nucleus to the thalamus and to the basal forebrain. The higher ketamine doses result in profound unconsciousness marked by electroencephalogram patterns, which show profound oscillations (0.1-1 Hz) alternating with gamma oscillations.

Each surgical insult induces local release of numerous inflammatory mediators, which entire the circulation and spread systematically. These inflammatory mediators are major amplifiers of the nociceptive response to the insult. One of the most prevalent of these mediators are the prostaglandins. Suppression of prostaglandin synthesis at sites of inflammation is the primary mechanism underlying the anti-nociceptive effects of NSAIDs. The anti-nociceptive and anti-inflammatory effects of NSAIDs result from their ability to inhibit the activity of the cyclooxygenase (COX) isoforms 1 and 2. Inhibition of the COX enzymes impairs the two-step transformation of arachidonic acid into prostaglandin and with this, the production of this key inflammatory mediator.

When used in nerve blocks or regional anesthesia, local anesthetics produce antinociception by either inhibiting excitation of nerve endings or by blocking conduction of action potentials in peripheral nerves. Local anesthetics accomplish these effects by binding reversibly to sodium channels and thus, blocking the sodium influx required to sustain action potentials. The primary target of the local anesthetic is the sodium channel open state and the effectiveness of the local anesthetic in blocking action potential propagation depends critically on how frequently the neuron is depolarized. Blocking of sodium channels is not likely to be the primary mechanism through which local anesthetic infusions contribute to anti-nociception because these effects are achieved at relatively low blood concentrations. A more likely mechanism is by their ability to block neutrophil priming. This G-protein mediated effect presumably impedes the ability of neutrophils to amplify the inflammatory response created by a surgical insult.

SUMMARY

During surgery, an anesthesiologist may rely on changes in heart and blood pressure, the epidemiologic profile of the patient, the pharmacology of the anesthetics being used, and previous experience with similar patients and similar surgeries to decide how and when anti-nociceptive agents should be administered to the patient. The anesthesiologist may also use the patient's respiratory rate to administer anti-nociceptive agents if the patient is not paralyzed. Post-operatively, an anesthesiologist may rely on the patient's subjective reporting of pain in addition to physiological responses such as heart rate and blood pressure. However, several confounding factors, including drug-induced hemodynamic instability, respiratory variability, and hypnotic effect make it difficult to track nociception, restricting an anesthesiologist's ability to predict the patient's underlying nociceptive state. As a consequence, patients are often grossly underdosed and suffer in pain, or are overdosed and remain sedated or delirious for many hours following surgery.

In particular, an anesthesiologist may use frequency-based metrics of heart rate variability (HRV) computed from the electrocardiogram (ECG) to estimate nociception. HRV, which can be computed from the ECG, is the beat-to-beat variation in the heart rate and is affected primarily by autonomic inputs, both sympathetic and parasympathetic. Common heart rate metrics include power in low (0.04-0.15 Hz) and high (0.15-0.4 Hz) frequency ranges (LF and HF, respectively). HF correlates with parasympathetic tone, while LF is thought to be a combination of sympathetic and parasympathetic tones. Derived measures, such as the ratio LF/HF or normalized values of LF and HF (LFu and HFu, respectively), are also used to estimate a person's SDAS. However, the unimodal nature of these indices can make them misleading, particularly in situations where the breathing rate causes respiratory sinus arrhythmia (RSA) to be a confounding factor.

In general, multimodal models are better than unimodal model because it is less likely to be swayed by one factor (e.g., drug class, signal processing step) that might affect one index or modality alone. A multimodal model can also capture more complementary information than unimodal models since different modalities have different strengths.

Moreover, multimodal models enable multimodal general anesthesia, which can be used to manage unconsciousness, antinociception, and akinesia separately but with an understanding of synergistic effects. Multimodal general anesthesia involves managing the different components of general anesthesia separately but with the understanding that most drugs affect more than one component. For multimodal general anesthesia to be most effective, each component should be tracked separately.

If an anesthesiologist could accurately and objectively quantify a patient's nociceptive state, the anesthesiologist could tailor the anesthetic strategy to maintain antinociception precisely. This would avoid the current tendency to overdose drugs in order to induce unconsciousness and antinociception. It could also reduce the possibility of inadvertently underdosing the patient and lead to a decreased reliance on opioids, possibly reducing the incidence of long-term dependence on or addiction to opioids among surgery patients. Other potential benefits include generally less drug used overall and better pain management.

The techniques disclosed herein can be embodied, for example, as a method of administering anesthetic agents to a patient. This method includes concurrently measuring a variability in electrodermal activity, heart rate, and heart rate variability of the patient with appropriate sensors. A processor coupled to the sensors determines a nociceptive state of the patient based on the variability in the electrodermal activity, the heart rate, and the heart rate variability and shows the results to a clinician via a display. And the clinician adjusts a dosage of an anesthetic agent administered to the patient based on the nociceptive state.

Another embodiment includes a method comprising: obtaining electrodermal activity and a variability in heart rate of the patient, then generating point process models of the electrodermal activity and the variability in the heart rate. These point process models are used to construct a quantitative multi-dimensional measure of a nociceptive state of the patient.

Yet another embodiment includes a method of analyzing electrodermal activity. In this method, a process receives data representing electrodermal activity of a subject. The processor isolates a tonic component from the data and determines a phasic component in the data based at least in part on the tonic component. The processor then extracts pulses from the phasic component of the data and determines a threshold for the at least one pulse based on a statistical distance. The processor uses this threshold to determine a distribution of inter-pulse intervals between consecutive pairs of the pulses. Then the processor analyzes a goodness-of-fit for the distribution based on a statistical distance plot.

Still another embodiment includes a method of tracking a nociceptive event of a patient. In this method, a processor receives a measurement indicating electrodermal activity of the patient. A low-pass filter, possibly implemented with the processor, identifies a tonic component from the measurement. The processor extracts a phasic component from the measurement based at least in part on the tonic component, then generates a point process model for the phasic component based on the phasic component. The processor tracks the nociceptive event based at least in part on the point process model.

A further embodiment includes a method of administering an anesthetic agent to a patient. This method includes obtaining electrodermal activity of the patient, extracting temporal and amplitude information from the electrodermal activity, and determining a nociceptive state of the patient based at least in part on the temporal information and the amplitude information of the electrodermal activity. This nociceptive state can be used to adjust a dosage of the anesthetic agent administered to the patient based on the nociceptive state.

A still further embodiment includes a method comprising obtaining electrodermal activity and a variability in heart rate of a patient and determining a measure of the variability in the heart rate of the patient. Next, a state space framework model is constructed based on the electrodermal activity of the patient and the measure of the variability in the heart rate of the patient. A sympathetic-driven arousal state is estimated based on the state space framework model.

And yet a further embodiment includes a method for estimating a sympathetic-driven arousal state in a patient. This method includes obtaining electrodermal activity and variability in heart rate of the patient. The electrodermal activity is used to determine a time-based measure and an amplitude-based measure of a variability in the electrodermal activity. These measures are used to generate first and second point process models, respectively. Likewise, variability in the heart rate is used to determine a frequency-based measure of the variability in the heart rate of the patient, which is used in turn to generate a third point process model. The first, second, and third point process models are used to construct a multimodal model, which is used to estimate the sympathetic-driven arousal state in the patient.

All combinations of the foregoing concepts and additional concepts are discussed in greater detail below (provided such concepts are not mutually inconsistent) and are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., elements that are functionally and/or structurally similar).

FIG. 3C is a segment of pre-processed phasic EDA data with tonic component subtracted from one subject labeled with traditional pulses and smaller micropulses.

FIG. 3D is a histogram of inter-pulse intervals for the EDA data in FIG. 3C.

FIG. 8A shows KS plots for re-scaled inter-pulse intervals compared to uniform distributions for EDA data from Subjects 1 and 2 using the optimal values for model order and window for local log-likelihood estimation FIG. 8B shows plots of correlation of consecutive original inter-pulse intervals (left) and rescaled inter-pulse intervals (right) for the EDA data from Subjects 1 and 2.

FIG. 8C shows autocorrelation plots for lags of up to 60 inter-pulse intervals.

FIGS. 9A-9E show the propofol sedation profile and point-process mean and standard deviations of EDA pulses for Subjects 1 and 2.

FIGS. 11A-11E illustrates a fourth subject's paced breathing task results, showing respirations (FIG. 11A), instantaneous heart rate plus and minus standard deviation (FIG. 11B), instantaneous estimates of LF (left axis) and HF (right axis) power (FIG. 11C), tonic (left axis) and phasic (right axis) EDA activity with labeled pulses (FIG. 11D), and SDAS estimates in a state space model with multimodal versus unimodal observations (FIG. 11E).

DETAILED DESCRIPTION

Figure 1A:
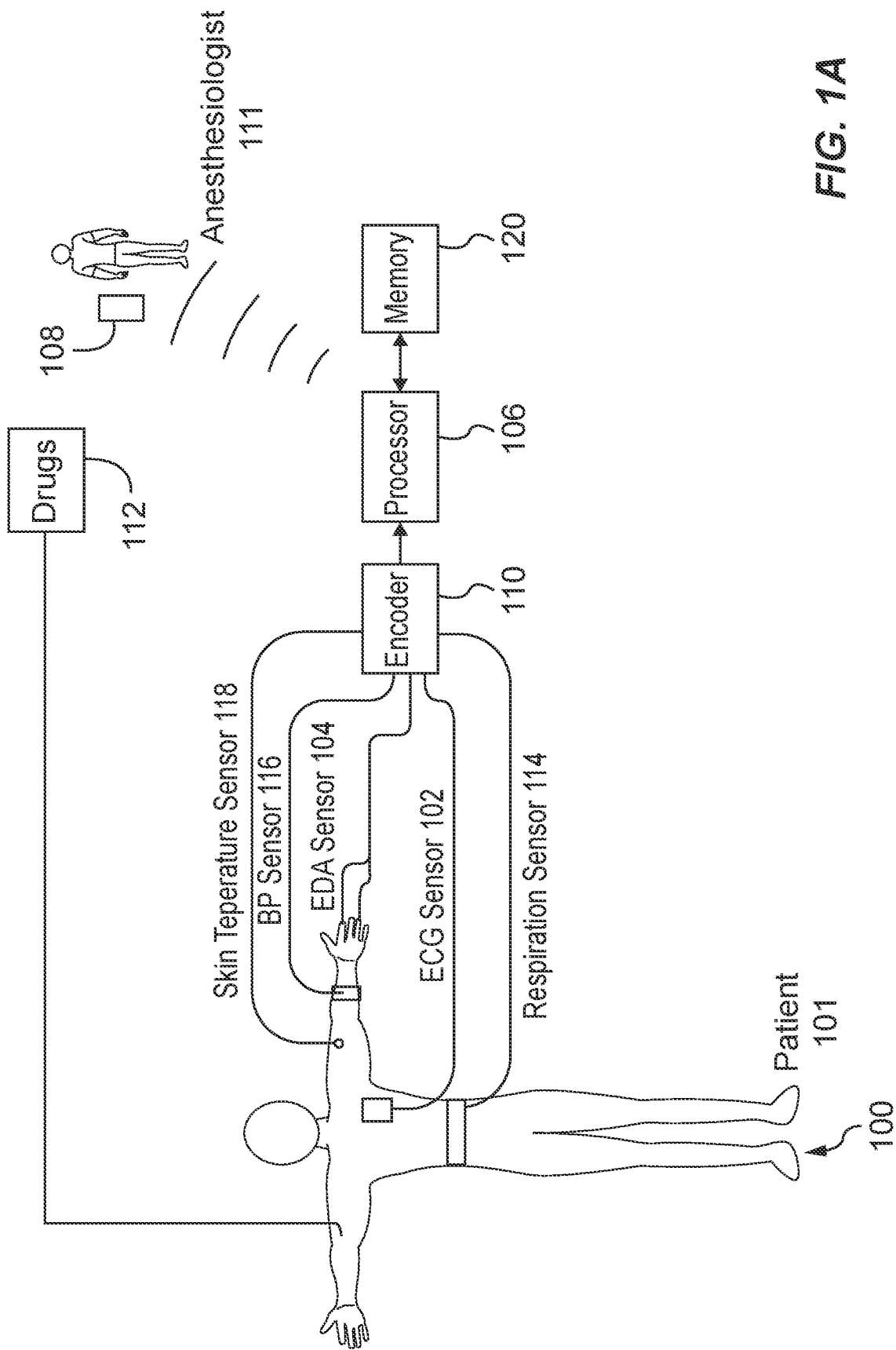
FIG. 1A shows a system for tracking nociception in a subject using a multimodal metric.

Conventional methods for tracking sympathetic-driven arousal state (SDAS), including nociception under anesthesia, have drawbacks, in part because of a lack of accurate measurements of nociception. Studies of nociception and pain usually include animal models or human studies that use paw pokes, surface incisions, or heat pain on the skin as painful stimuli. However, none of these models depicts surgical nociception accurately.

Surgical nociception typically results from the cutting of skin, tissues, and organs and the resultant autonomic, inflammatory, and stress responses. One way to capture the nociceptive insult that occurs during surgery is to record data during surgery itself. However, previous attempts to quantify surgical nociception using quantitative indices only brought these measures to the operating room when it was time for validation. These previous indices were devised independently using non-surgical pain data or just a heuristic understanding of the signals at hand.

More specifically, previous attempts at tracking or measuring nociception in the operating room (OR) suffer from one or more of the following flaws or drawbacks: (1) using only one physiological signal, such as only ECG or only electrodermal activity (EDA); (2) applying a machine learning method to a single limited dataset without an underlying physiological model; (3) relying on heuristic without theoretical explanation; and (4) being validated in limited patient populations or using only one class of drugs. For example, some previous models are unimodal models that rely solely on frequency-based heart-rate variability (HRV) measures. However, these unimodal models overestimate SDAS during the slowest breathing stage and underestimate it in subsequent stages. Under general anesthesia, in many cases the patient is on a ventilator because they are given muscle relaxants. In the OR, some of the frequency-driven HRV metrics can be influenced by the breathing rate set on the ventilator, which makes unimodal metrics based on HRV misleading when taken alone.

In contrast to existing methods of tracking nociception, the multimodal approaches disclosed here for tracking nociception are computationally less expensive, more statistically rigorous, and provide more accurate and robust results. These multimodal approaches are based on the observation that a nociceptive surgical stimulus initiates an increase in sympathetic output and a decrease in parasympathetic output through the nociceptive-medullary-autonomic (NMA) circuit. The increase in sympathetic output and a decrease in parasympathetic output are manifested as an increase in heart rate, an increase in blood pressure, and an increase in EDA. The technology disclosed here provides more accurate tracking of nociception of a patient under anesthesia because it uses multiple physiological signals, including combinations of EDA, heart rate (HR), HRV, and, for patients with arterial lines, blood pressure (BP), instead of a single physiological signal. This technological improvement makes it possible to tailor the anesthesia more precisely, reducing the risk of overdosing or underdosing opioids or other drugs.

In contrast, other EDA-based models are neither statistically rigorous nor well-validated. EDA is typically measured from two electrodes placed on the hand and tracks the changes in electrical conductance of the skin due to pulsatile rise of sweat to the skin surface. It is solely sympathetically controlled. Other EDA models include both metrics such as number of fluctuations in skin conductance (NFSC) and more complex deconvolution processes. NFSC-based methods are based on measuring the number of oscillations in EDA that are larger than a set threshold (attempting to capture GSRs) averaged across time. While easy to calculate, NFSC-based methods do not return truly instantaneous estimates of sympathetic activity and require setting an arbitrary threshold.

Deconvolution-based methods assume that the underlying sudomotor nerve input to the sweat gland can be deconvolved from EDA using a single impulse response function representing the GSR or a single "pulse." However, these approaches make unverified physiological assumptions and cannot fully reconstruct EDA. Deconvolution-based methods cannot account for intra-subject variation in the shape of EDA, suggesting that the underlying physiological assumption is incorrect, and the resulting estimate for neural activity cannot be validated. In addition, deconvolution is computationally expensive, because both the deconvolved output and the impulse response function must be estimated at each time point. It is also sensitive to initial choice of parameters.

Tracking Nociception in an Anesthetized Patient

Figure 1B:
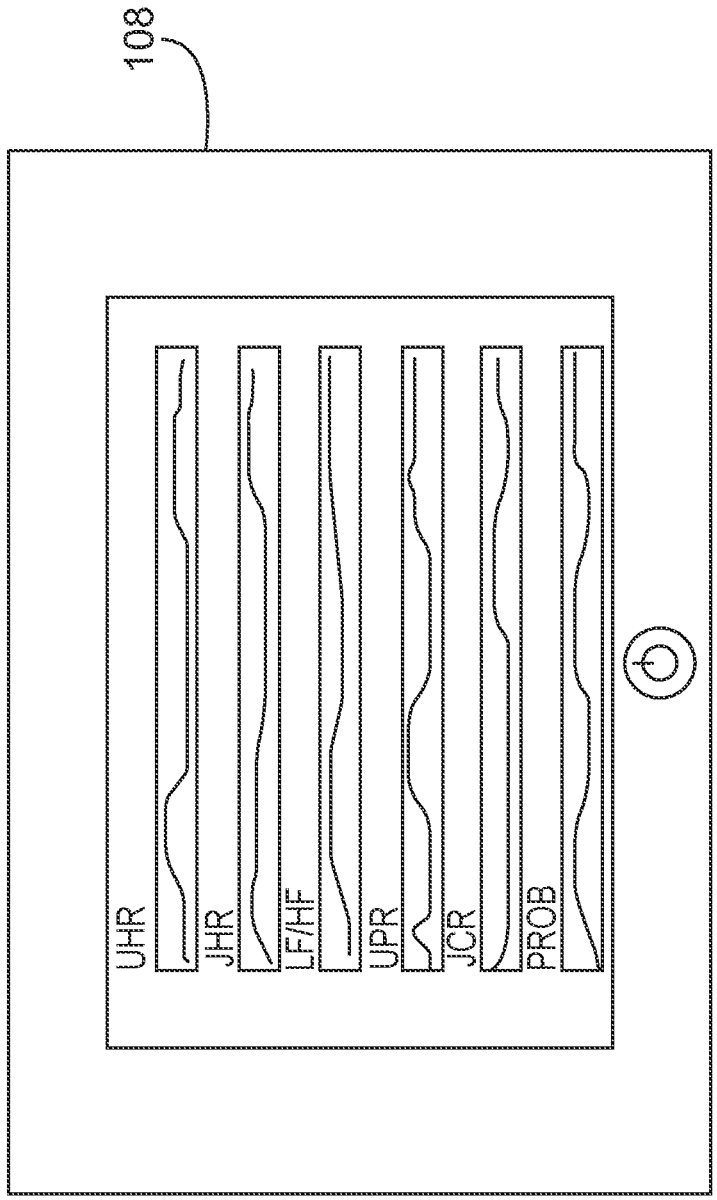
FIG. 1B shows a display of the system of FIG. 1A.

FIGS. 1A and 1B depict a system 100 for tracking nociception in a patient 101 under anesthesia using a multimodal metric in accordance with some inventive aspects. The system 100 includes a heart rate (HR) sensor 102, such as an ECG or pulse pressure wave sensor, and an EDA sensor 104, which may be coupled or attached to the patient's fingers. The system 100 may also include a respiration sensor 114, blood pressure (BP) sensor 116, skin temperature sensor 118 (e.g., close to the EDA sensor 104), which are coupled to an optional encoder 110 along with the HR sensor 102 and the EDA sensor 104. The sensors can be grouped together, e.g., with electrodes or sensing elements that are grouped together in a first patch on the patient's chest and a second patch on the patient's wrist. The sensors can be wirelessly coupled to the processor 106 and synchronized to each other or to the same clock (e.g., a separate reference or the processor's internal clock). The sensors and processor 106 should not interfere with each other or with any of the other equipment used in the operating room during surgery.

The encoder 110 is coupled to and feeds data from the sensors (including the HR sensor 102 and the EDA sensor 104) to a processor or controller 106, which is coupled in turn to a display 108 and non-volatile memory 120, which stores sensor data and computer-executable instructions for processing the sensor data as described below. The display 108 may be integrated with the processor 106 or it may be a separate device, such as a smartphone or a tablet. The HR sensor 102, EDA sensor 104, processor 106, and display 108 may be coupled to each wirelessly (e.g., via Wi-Fi or Bluetooth connections) or with appropriate wires or cables. They can also be integrated together into a single device.

The HR sensor 102 can be implemented as any suitable device that can obtain HR, HR variability, electrocardiogram (ECG) data, and/or pulse plethysmography data from the patient 101. For instance, the HR sensor 102 can be a wearable device, such as a deflection sensor worn around the patient's torso. Suitable HR sensors 102 include wearable body sensors with self-adhesive electrodes such as the Savvy™ sensor, bio sensors such as the SEEQ™ sensor, ZIO® XT Patch, Philips® biosensor, and/or the like. The HR sensor 102 includes three to twelve electrodes to measure ECG data and relays the collected data in real time to the processor 106 for time-locking/synchronization with the EDA data.

The HR sensor 102 can acquire HR data from the patient 101 at a sampling rate of 100 Hz or more. If implemented as an ECG sensor, it may have at least three electrodes distributed in some fashion around the patient's heart. The electrodes can be combined into a single patch. ECG electrodes are usually "wet"—they are coated with an adhesive or gel—but they are the standard silver/silver-chloride electrodes used for many physiological measurements (ECG, EMG, etc.). There are also dry electrodes (no gel or adhesive), but they have much higher impedance and should maintain strong contact for good signal quality.

The HR sensor 102 can also be implemented as a pulse pressure wave sensor on the patient's finger. The peaks of the pulse pressure wave correspond to R peaks in the ECG but with a delay, so they can still be used to extract the same information. They can also be useful to help 'fill in' ECG data if there are artifacts in the ECG data. Using the pulse pressure wave from the finger may allow for all the sensors to implemented in a single device on the hand (HRV and EDA), which is convenient for cardiac surgery, for example, where access to the chest for electrode placement may be limited.

The EDA sensor 104 measures the patient's EDA and EDA variability, or, more specifically, variability in the patient's skin conductance. The EDA sensor 104 can placed on the patient's finger(s), wrists(s), or on the sole(s) of a patent's foot. There are two general types of EDA sensors 104, based on two different EDA sensing methods-endosomatic and exosomatic. An exosomatic sensor applies an external alternating current (AC) or direct current (DC) to the patient's skin. Most EDA devices 104 make exosomatic DC measurements. EDA electrodes can also be either wet or dry. In both cases, strong contact should be maintained to ensure good signal quality.

FIG. 1B shows a monitor (e.g., display 108) with several traces in real time or as close to real-time as possible as collected by the system 100 of FIG. 1A. The top four to five traces are the physiologic indices, such as HRV and EDA indices. The bottommost trace is the probability of patient perceiving nociception at that time between 0 and 1. This probability of patient perceiving nociception is computed from the others metrics as described below. Displaying all of the information can be helpful for the anesthesiologist 111.

Figure 2A:
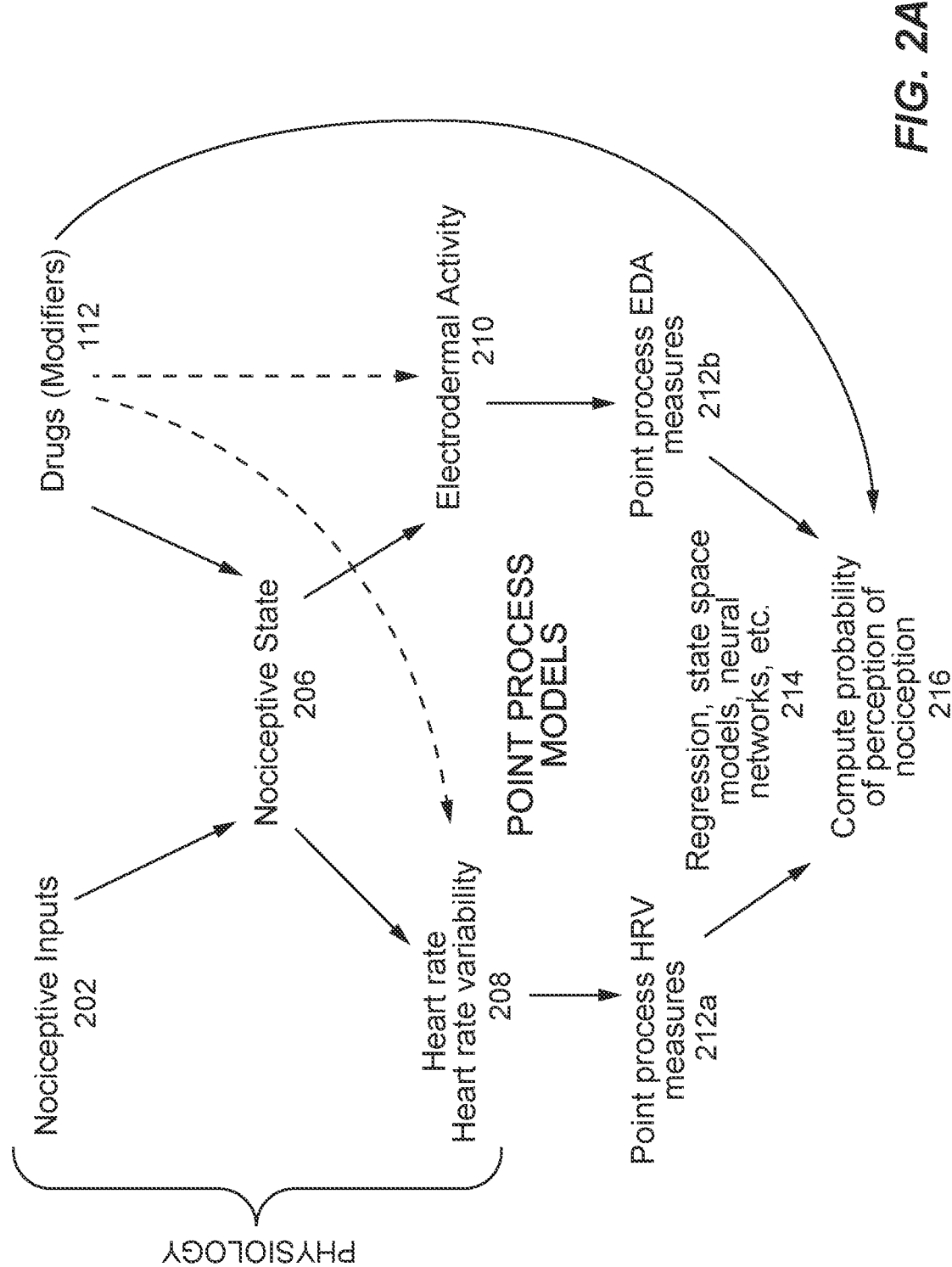
FIGS. 2A and 2B illustrate a method for tracking nociception in a subject using a multimodal metric.
Figure 2B:
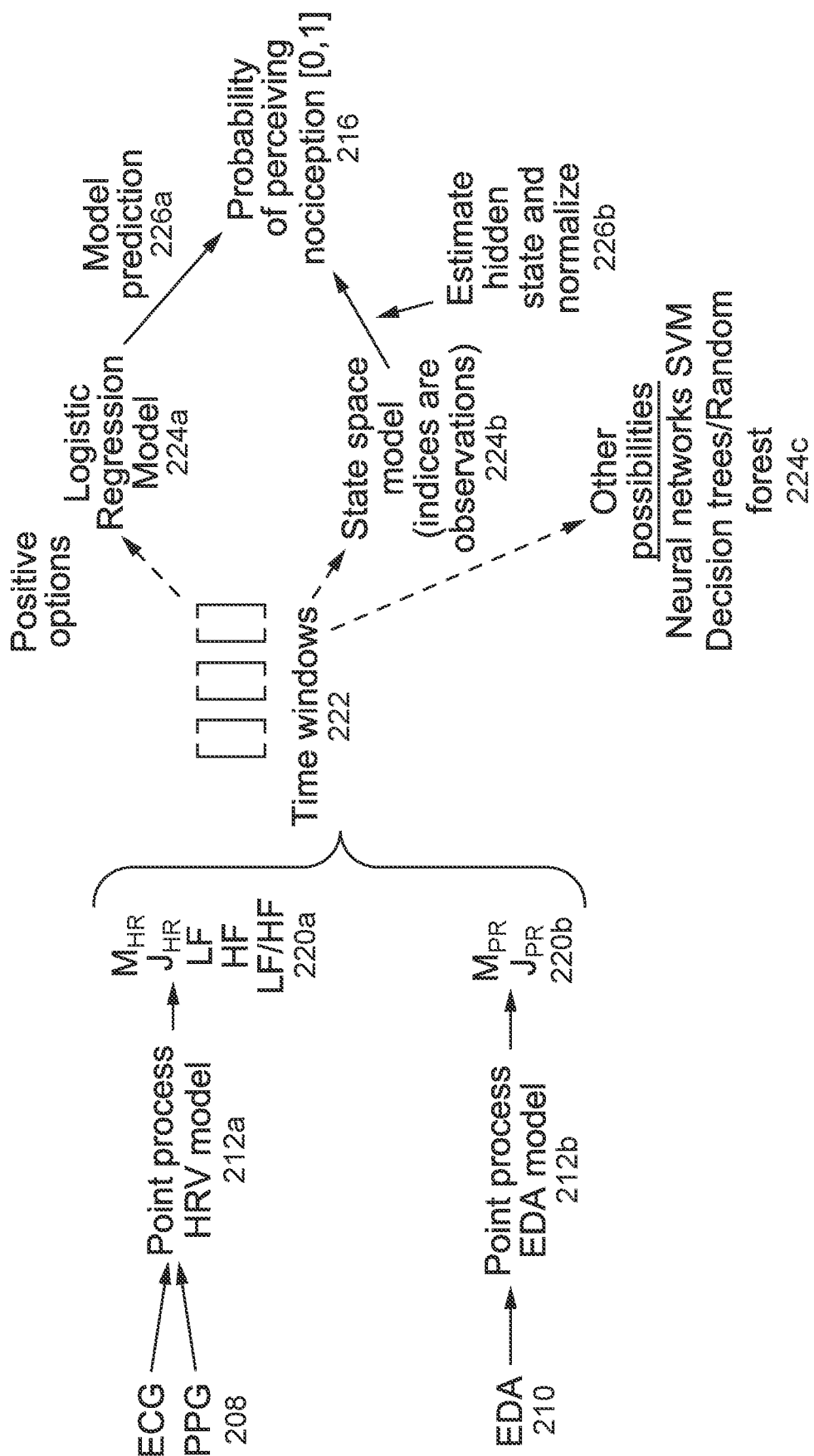

FIGS. 2A and 2B illustrate how to use the system 100 of FIG. 1A for tracking the nociceptive state 206 of the patient 101. The patient's nociceptive state 206 depends on a variety of physiological nociceptive inputs 202, such as temperature, movement, and pressure as sensed by the patient 101, as well as drugs 112 and other modifiers administered by the patient's anesthesiologist 111. The patient's nociceptive state 206 manifests itself in both the patient's HR and HR variability 208 and EDA 210.

The HR sensor 102 measures the patient's HR and HR variability 208 while the EDA sensor 104 measures the patient's EDA 210. The sensors send these data to the processor 106 in real-time, which transforms the HR and HR variability 208 and EDA 210 into HR point process data 212a and EDA point process data 212b, respectively (collectively, point process data 212). The processor 106 uses the point process data 212 and regression, state-state models, neural networks, and/or other statistical frameworks 214 to compute a probability of the patient's perception of nociception 216. The processor 106 performs this processing in real-time or with lag of at most few seconds.

In particular, the processor 106 uses a point process model to capture the autonomic dynamics in EDA and ECG or pulse pressure wave data without having to estimate the underlying neural input. First, the processor 106 may identify whether there is statistical structure in EDA or HRV data. Then the processor 106 uses the identified structure to construct a point process model for instantaneous dynamics as explained in greater detail below. The processor 106 can display an indication (e.g., as in FIG. 1B) of the resulting probability of the patient's perception of nociception 216 to an anesthesiologist 111. This indication may take the form of a graph or trace of the probability of patient perceiving nociception along with some of the HRV and EDA indices, such as mean+/−standard deviation for HR, EDA, frequency-based HRV metrics, including LF, HF, LFu, HFu, and LF/HF.

The anesthesiologist 111 can respond to this indication by adjusting the type and dosage(s) of the drug(s) 112 administered to the patient 101. Because the indication of the probability of the patient's perception of nociception 216 is more accurate than indications provided by unimodal approaches, the anesthesiologist 111 can tailor the drug regimen more effectively, thereby reducing or eliminating side effects caused by overdosage or underdosage of the drugs 112. Too much anesthetic can cause confusion, nausea, and vomiting upon reawakening and difficultly urinating and defecating. Too little anesthetic can cause persistent or intermittent pain for months to years after surgery, which in turn can lead to dependence on or addiction to opioids. And too much or too little anesthetic can lengthen the patient's postoperative stay in the hospital, driving up healthcare costs.

To avoid these complications, the anesthesiologist 111 may use the more precise indication of nociception 216 provided by the system 100 to administer a combination of drugs 216 selected to reduce transmission in nociceptive pathways and decrease arousal and perception of nociceptive stimuli instead of simply increasing the quantity of propofol or opioid. (Propofol is an anesthetic given intravenously and acts as a GABA-A agonist. There are specifically many GABA-ergic inhibitory interneurons present throughout the arousal circuits in the pons, midbrain, hypothalamus, and basal forebrain and its action in these areas is thought to be the primary reason for its role in inducing and maintaining unconsciousness during general anesthesia.) For example, the anesthesiologist 111 may administer a combination of ketamine, dexmedetomidine, lidocaine, NSAIDs, and regional blocks instead of an opioid like dilaudid during surgery. After surgery, the patient 101 can take NSAIDs to reduce pain and inflammation instead of more opioids for pain management and other drugs to reduce the side effects of the opioids.

FIG. 2B shows a process to arrive at a computed probability of perception of nociception starting with raw ECG or pulse plethysmography (PPG) data 208 and raw EDA data 210. This process describes the directly observable portion of the flowchart shown in FIG. 2A, from heart rate and heart rate variability 208 and EDA 210 through probability of perception of nociception 216. (The top portion of FIG. 2A is physiology that cannot be directly observed using presently available techniques.)

The point process models for HRV 212a and EDA 212b are applied to the ECG data 208 and EDA data 210, respectively, to yield point process HRV 220a and EDA indices 220b (collectively, point process indices 220). These point process indices 220 are computed as instantaneous estimates and then combined into time windows 222 of a specified length. These time windows 222 can then be processed in one of a variety of statistical models to yield a probability of perceiving nociception 216. This probability 216 can be presented using a continuous scale ranging from 0 to 1 or any other suitable scale (e.g., 0% to 100%).

These statistical models include a logistic regression model 224a, in which the model prediction 226a itself is a value between 0 and 1. Another statistical model is a state space model 224b where the point process indices 220 in time windows 222 are the observations and the goal is to estimate a hidden state 226b. By normalizing the hidden state 226b, a value between 0 and 1 that signifies probability of perceiving nociception 216 can be achieved. Other possible statistical models include neural networks, support vector machines, and decision trees 224c, all of which return outputs that can be normalized to values between 0 and 1. Each of these statistical models has various strengths and weaknesses, between interpretability, flexibility to match physiology, and computational efficiency.

The processes shown in FIGS. 2A and 2B are more computationally efficient and more realistic than existing processes. Most existing HRV models and some EDA models are very heuristic based and therefore might be simple but are not accurate physiological representations. Many popular EDA models are based purely on signal processing precedent from different domains. They have many parameters that have to estimated, which is computationally intense. The EDA model presented here uses distributions that are one to three parameter models, and so even with dynamic autoregressive coefficients, they are much less complex—and therefore computationally more efficient—than EDA models based on deconvolution. This huge reduction in complexity accompanies much higher accuracy because the parameters used in the EDA model presented here are relevant to physiology rather than based purely on signal processing.

Examples of Monitoring Consciousness and Nociceptive State

General anesthesia is a drug-induced reversible state comprising antinociception, unconsciousness, amnesia, and muscle relaxation with maintenance of physiological stability. An anesthesiologist administers a combination of drugs to achieve the state of general anesthesia. The anesthesiologist may use a standard paradigm to track a patient's state of general anesthesia. Every 1 to 3 minutes, the anesthesiologist makes a continual assessment of the patient's physiologic state, antinociceptive state and state of unconsciousness. The anesthesiologist assesses the patient's physiological state by evaluating the markers: heart rate, blood pressure, oxygen saturation, core temperature, and level of muscle relaxation. In response to The antinociceptive state can be tracked by the measures (indices) of antinociception provided by the process and system described with respect to FIGS. 1A, 1B, 2A, and 2B. The anesthesiologist tracks the state of unconsciousness by EEG measures and indirectly by the markers of physiological state. Here are three example scenarios.

1. Scenario 1: Under general anesthesia maintained with propofol as the primary hypnotic (unconsciousness-producing) agent, the system detects a transition from slow-delta oscillations (0.1 to 4 Hz) and alpha oscillations (8 to 12 Hz) to beta oscillations (13 to 25 Hz), suggesting that the patient is passing to a lighter level of unconsciousness. There is no change in any of the physiological variables nor in the measures of antinociception. The system presents this data to the anesthesiologist, who uses the data to infer a decline in the patient's level of unconsciousness and administers more propofol or another appropriate agent to deepen the level of unconsciousness.

2. Scenario 2: The system detects and indicates a change in the patient's antinociceptive indices, suggesting that the patient is receiving more nociceptive stimulation. The system also detects and displays a slight increase in heart rate and blood pressure. The other physiological markers are unchanged and there are no EEG changes suggestive of a change in level of unconsciousness. From these indications, the anesthesiologist determines that the primary change in the patient's state is a decline the patient's level of antinociception and administers one or more agents to control nociception.

3. Scenario 3: Consider scenario 2 where, in addition to the changes in the indices of antinociception, propofol is being administered as the primary hypnotic agent and the system detects and indicates a transition from slow-delta oscillations (0.1 to 4 Hz) and alpha oscillations (8 to 12 Hz) to beta oscillations (13 to 25 Hz). As in scenario 1, this suggests that the patient is passing to a lighter level of unconsciousness as well. The anesthesiologist identifies the likely causal event when he notices that the surgeons stimulated the patient substantially by changing abruptly the position of the retractors. These observations suggest that there is a decline the patient's level of antinociception and a decline in the patient's level of unconsciousness. The anesthesiologist is administers an agent to increase the patient's level of antinociception. This alone may be adequate as these agents also increase level of unconsciousness. If solo administration of the antinociceptive agents is inadequate to also increase the level of unconsciousness, i.e., the beta oscillations persist, then the anesthesiologist can administer a hypnotic agent, such as propofol or sevoflurane, to increase the patient's level of unconsciousness.

For scenario 1, the information from the system's antinociception indices allows the anesthesiologist to infer that the primary issue is a declining level of unconsciousness. The system allows the anesthesiologist to appreciate that there is no nociceptive component to the change in level of unconsciousness. Similarly, the information provided by the system in scenario 2 allows the anesthesiologist to infer that the primary issue is a declining level of antinociception. Without the system, a common practice in scenario 2 would be to interpret the changes in heart rate and blood pressure as a decrease in level of unconsciousness and to administer a hypnotic agent, particularly in the absence of EEG recordings. That is, generally, little effort is made to distinguish changes in level of nociception from changes level of unconsciousness. The information provided by the system in scenario 3 makes clear that the primary event is an increase in nociceptive stimulation. Because the decline in antinociceptive level also induced a decline in the level of unconsciousness, the primary therapy should be administration of antinociceptive agent(s) followed closely by a hypnotic agent. In each scenario, the system provides the anesthesiologist a clear framework for reasoning about antinociceptive state of a patient and distinguishing changes in level of antinociception from changes in level of unconsciousness.

The following table shows three additional scenarios using the system of FIGS. 1A and 1B:

| Scenario 4 | Scenario 5 | Scenario 6 |
|---|---|---|
| HRV | HRV | HRV |
| MuHR <65 bpm for last 10 min SigmaHR >4 bpm for last 10 | MuHR increased from 70 to 80 bpm in last 5 min | MuHR increased from 65 to 80 bpm in last 5 min |

-continued

| Scenario 4 | Scenario 5 | Scenario 6 |
|---|---|---|
| min<br>EDA<br>MuPR <10 pulses per min for last 10 min<br>SigmaPR <5 pulses per min for last 10 min<br>Prob of perception of nociception <0.5 for last 10 minutes<br>EEG<br>Remains unchanged | SigmaHR decreased from 4 to 2 bpm in last 5 min<br>LF increased in last 5 min<br>HF has increased less than LF<br>EDA<br>MuPR increased from 15 to 35 in last 5 min<br>Sigma PR increased from 4 to 10 in last 5 min<br>Prob of perception of nociception increased from 0.5 to 0.7<br>EEG<br>Remains unchanged | LF increased in last 5 min<br>EDA<br>MuPR increased from 15 to 18 pulses per min in last 5 min<br>Bolus of ephedrine was given 5 min ago<br>Prob of perception of nociception increased from 0.4 to 0.55<br>EEG<br>Remains unchanged |
| Do nothing<br>Continue to monitor | Manage nociception<br>For example, bolus dose of opioid | Continue to monitor closely<br>If Prob continues to increase over the next 5 minutes (and EDA activity increases specifically), consider managing nociception actively |

In scenario 4, the point process mean heart rate (muHR) has been steadily under 65 beats per minute (bpm) for the past 10 minutes. The point process standard deviation of heart rate (sigmaHR) has been above 4 bpm for the past 10 minutes. The point process mean pulse rate of EDA (muPR) has been under 10 pulses per minute and the point process standard deviation of heart rate (sigmaPR) has been under 5 pulses per minute for the past 10 minutes. The computed probability of perception of nociception has been under 0.5 for the past 10 minutes. All of this would indicate a stable and low nociceptive state. The EEG has also been stable for the past 10 minutes, indicating a stable level of unconsciousness. In this case, since there is no need to address either changing consciousness or nociceptive state, a clinician would not administer any drug and just continue to monitor the patient's consciousness and nociceptive state.

In scenario 5, in the past 5 minutes, muHR has increased from 70 to 80 bpm and sigmaHR has decreased from 4 to 2 bpm. The frequency domain HRV index of LF, which indicates a combination of sympathetic and parasympathetic activity has increased, while HF, which indicates parasympathetic activity primarily, has increased less than LF. muPR and sigmaPR have both increased from 15 to 35 and 4 to 10 pulses per minute, respectively. And while the EEG activity remains unchanged, the probability of perception of nociception has increased from 0.5 to 0.7. The lack of marked change in EEG indicates a stable level of unconsciousness. However, the other autonomic markers indicate increased nociceptive state showing greater sympathetic response. Since no drug has been administered in the past 5 minutes, and the patient is not bleeding out, this is likely due to increased nociception. This can be confirmed by noticing that the surgeons are stretching and cauterizing tissue repeatedly. The clinician should manage the nociception directly, for example, by administering a bolus dose of an opioid.

In scenario 6, once again the EEG remains unchanged over the past 5 minutes. muHR has increased from 65 to 80 bpm, while LF has increased. muPR has increased from 15 to 18 pulses per minute. The probability of perception of nociception has increased from 0.4 to 0.55 in the past 5 minutes. Unlike in scenario 5, however, the patient was just given a bolus dose of ephedrine, a sympathomimetic drug given to maintain blood pressure. The lack of change in EEG indicates stable level of unconsciousness. There are some autonomic changes that indicate increased sympathetic activity; however, in this case there is a clear reason to expect these changes—the sympathomimetic drug. In addition, ephedrine should have stronger effects on HRV rather than EDA indices, since it acts directly on the heart and blood vessels, and this seems to be the case. If there is no specific change in the surgery that could lead to increased nociception, the clinician may choose to not give any additional drug at this moment but should continue to monitor the patient closely. If the patient's probability of perception of nociception declines over time, then no action is necessary. However, if the patient's probability of perception of nociception continues to increase, and especially if the EDA activity also shows marked changes consistent with increased nociception (confirmed by observation of the surgeons' activity), nociception may be managed directly as in scenario 5.

Electrodermal Activity (EDA) and Galvanic Skin Responses (GSRs)

EDA captures changes in skin conductance that result from the activity of sweat glands. Having evolved as part of the "fight-or-flight" response, EDA is unique among autonomic markers in that it is solely under control of the sympathetic system. In addition, EDA can be measured easily, e.g., with a few electrodes on the fingers. To date, however, EDA's use in research and clinical medicine has been limited due to the lack of accurate statistical characterization based in physiology.

Figure 3A:
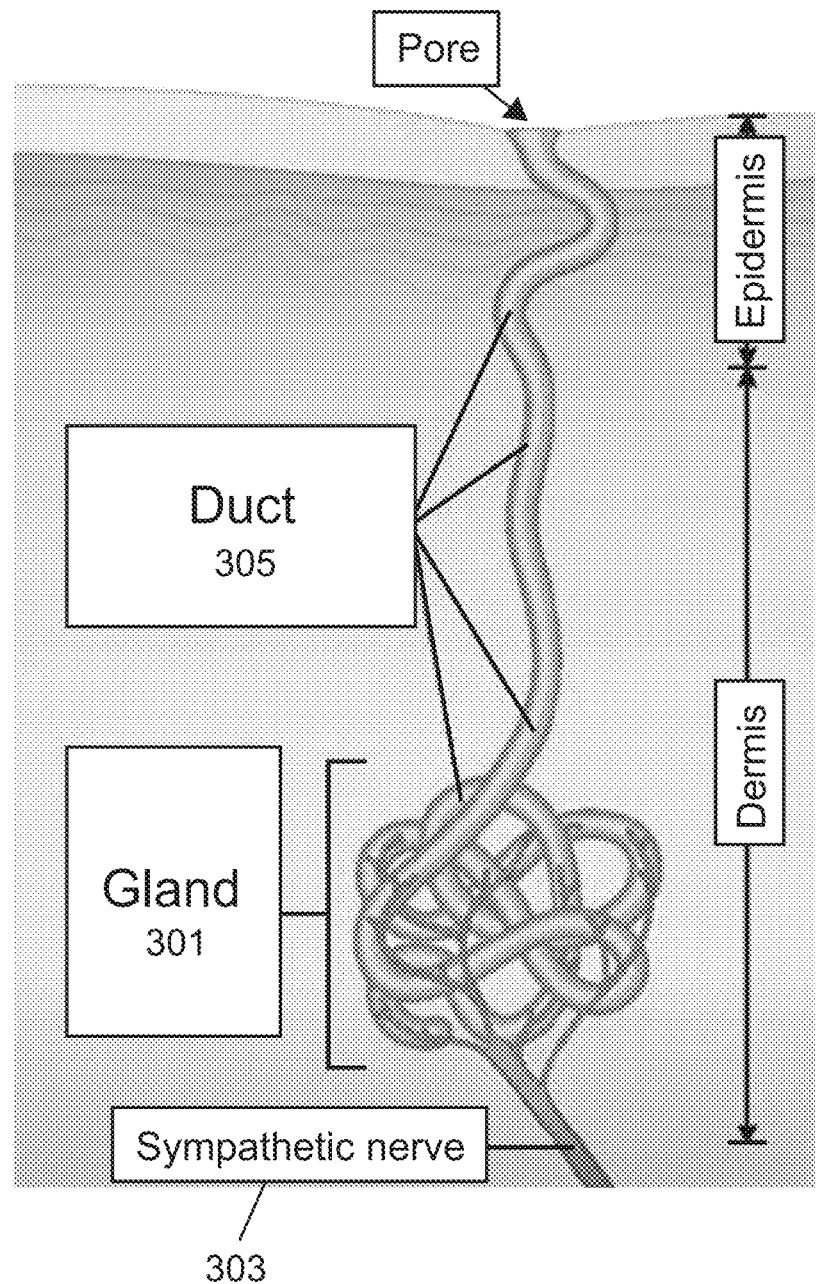
FIG. 3A illustrates increased firing of a sweat gland due to sympathetic activity.

FIG. 3A illustrates how increased firing of a sweat gland 301 due to sympathetic activity produces EDA. When the sudomotor nerve 303 which innervates the sweat gland 301 increases firing due to sympathetic activity, the sweat gland 301 secretes sweat, which diffuses upwards through the duct 305 of the sweat gland 303 towards the skin surface (epidermis 307). The diffused sweat creates a low resistance path through the skin (epidermis 307 and dermis 309), which results in an increase in skin conductance. The increase in skin conductance, which is called the galvanic skin response (GSR), is transient because the sweat evaporates gradually upon exposure to the air.

Figure 3B:
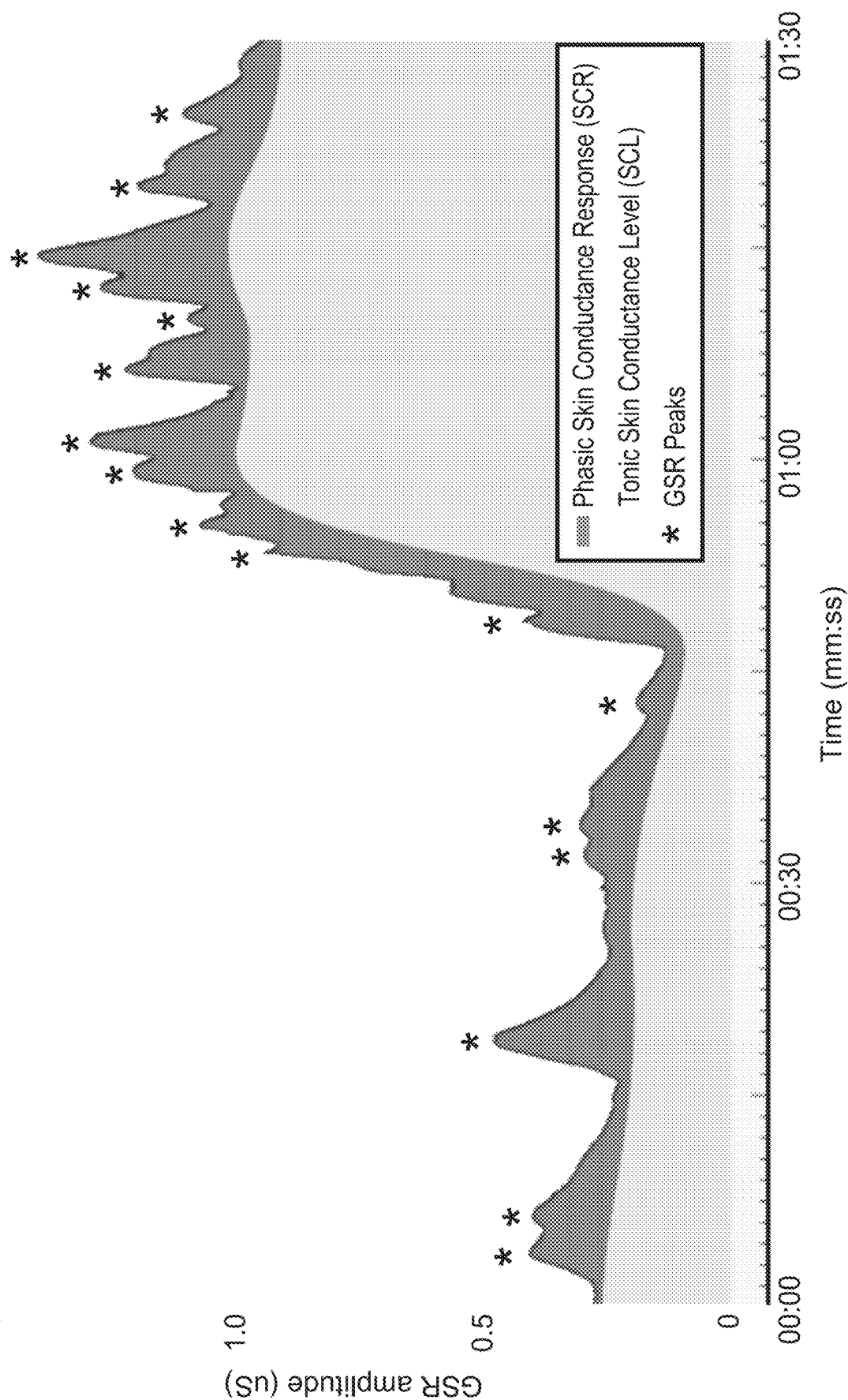
FIG. 3B is a plot of notional EDA showing phasic and tonic components and galvanic skin response (GSR) peaks.

FIGS. 3B-3D illustrate EDA data. FIG. 3B is a plot of notional EDA data showing the GSRs, which are marked by asterisks. The GSRs appear as pulse-like discrete rises and falls and are part of the phasic component of EDA. These GSRs, as well as smaller micropulses, are labeled in FIG. 3C, which shows the phasic component of measured EDA data. FIG. 3D is a histogram of the intervals between pulses in FIG. 3C. The phasic component correlates with sympathetic activity, as opposed to the EDA's tonic component, which represents evolution of the skin conductance level on a much slower time scale. Measured EDA typically aggregates the activity of several hundred sweat glands, each producing discrete GSRs due to nerve firing.

EDA Point Process Models

Unlike other methods, point process models EDA account for both the presence of discrete events in EDA data (e.g., GSRs) and for structure in the time intervals between these discrete events. Point process models can be binary stochastic processes in continuous time that can account for structure in the time intervals between these discrete events, such as GSRs. A GSR is a discrete event that occurs at a specific point in time, so it can be used as the basis for a point process model of EDA.

Figure 4:
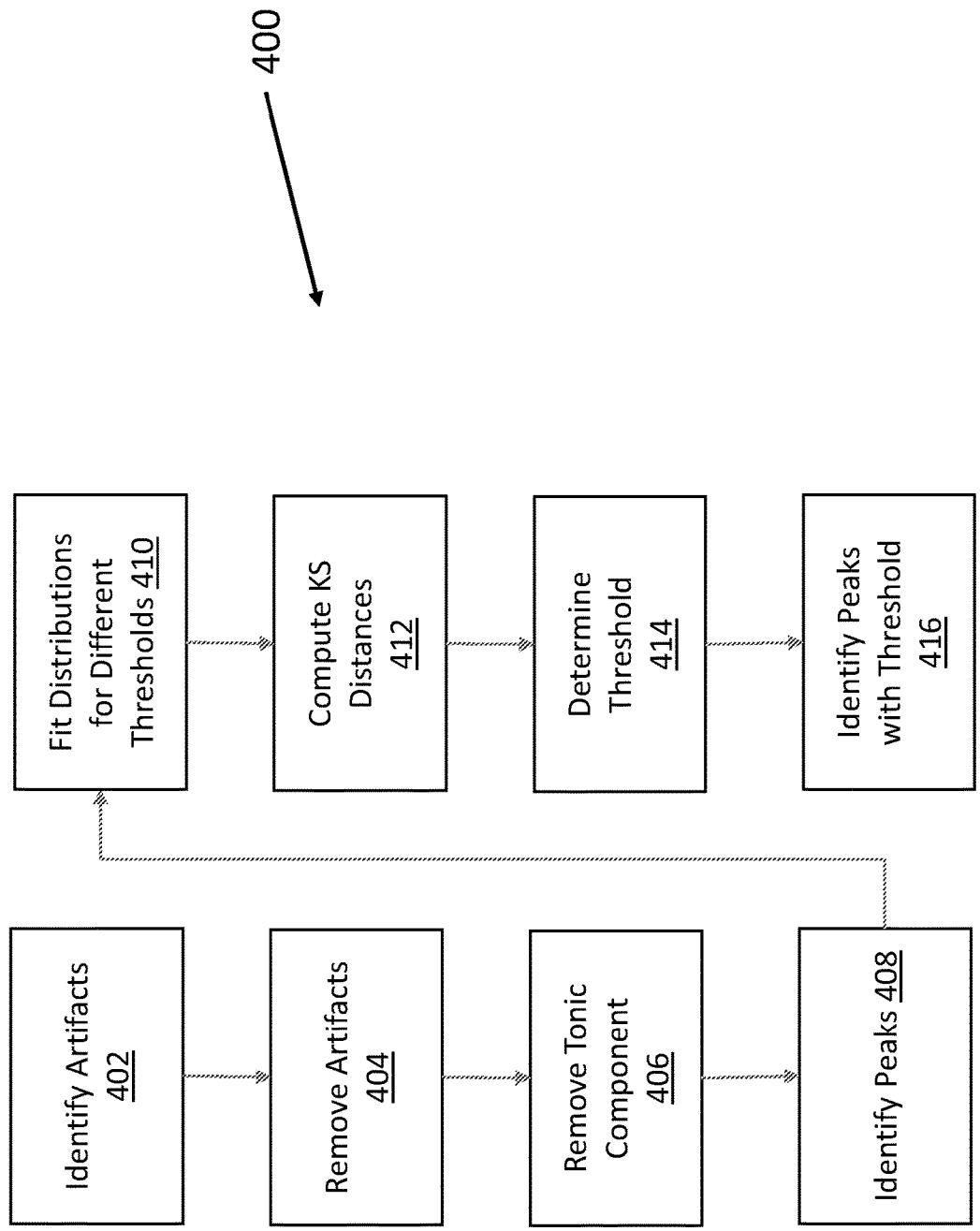
FIG. 4 illustrates a method of pre-processing electrodermal activity (EDA) for assessing nociception and other sympathetic-driven arousal states (SDASs).

FIG. 4 illustrates a method 400 for pre-processing EDA data using a suitable processor (e.g., the processor 106 in the system 100 of FIG. 1A). First, the processor detects artifacts by identifying large, sharp drops or rises in the data, defined as when the absolute value of the derivative of the signal exceeded 10 (step 402). Since it is physiologically impossible for sweat glands to activate that quickly and on that scale, the processor can easily isolate what are likely motion- or pressure-related artifacts. These artifacts were corrected by vertically shifting the data after each such artifact to match with the data beforehand and interpolating the few seconds of signal around the drop or rise itself with a cubic spline or interpolation using expectation-maximization (step 404).

Figure 5A:
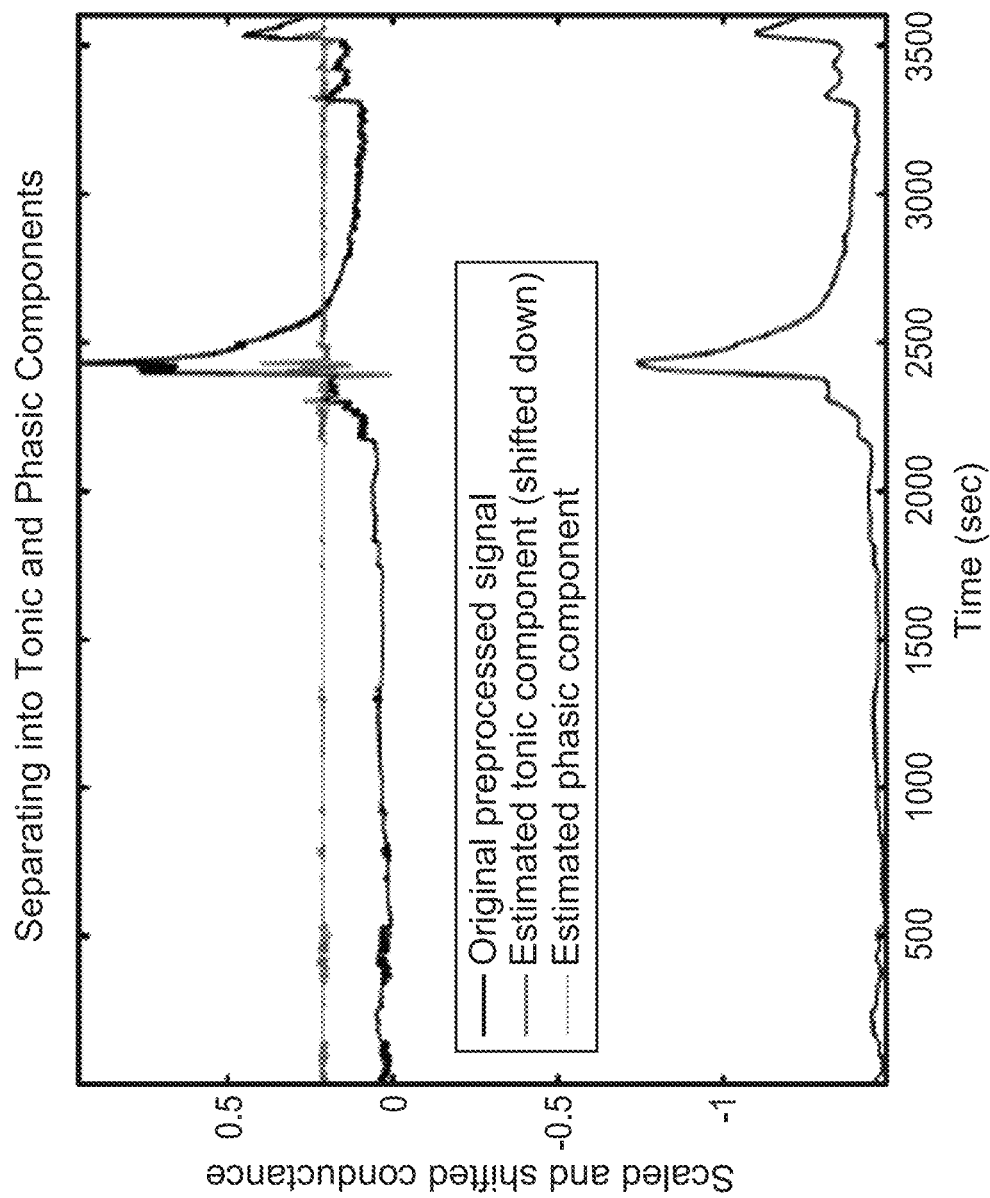
FIG. 5A illustrates the separation of tonic and phasic components from artifact-removed EDA data.

Next, the processor isolates and removes the tonic component of the data to leave only the phasic component, which contains sympathetic dynamics (step 406). To estimate the tonic component of the data, which is known to change on the order of several minutes, the processor can apply a finite impulse response (FIR) low pass filter with cutoff around $10^{-12}$ Hz and filter length of 8192 samples. Then the processor subtracts the estimated tonic component from the overall signal to yield the phasic component. FIG. 5A shows the decomposition of EDA data for one subject into phasic and tonic components. The tonic component is shifted down on the y-axis for ease of visualization.

The processor identifies peaks in the tonic component next. Most peak-finding methods rely on looking for points that are above a universal threshold. However, setting the threshold captures more noise, whereas setting the threshold too high can leave out tonic firing activity. In addition, the amplitudes of the GSR pulses change with background skin resistance level. As a result, pulse amplitudes can vary drastically not only between subjects, but even within a single subject across time.

To avoid these problems, the processor extracts pulses from the phasic component of the EDA data by finding peaks (local maxima) based on prominence (step 408), which accounts for local context around each peak. For each identified peak, the processor calculates prominence (step 410) by first drawing a horizontal line from the peak on either side and determining at what distance the line either intersects with the signal again or reaches one of the endpoints of the signal. Then, for that interval on either side of the peak, the processor finds the minimum value of the signal (a valley). The prominence of the peak is the height of the peak computed from the larger of the two valleys (one on either side of the peak). The processor uses the calculated peak prominences to determine an appropriate threshold for prominence.

To determine the appropriate prominence threshold for identifying the peaks, the processor fits several distributions (e.g., inverse Gaussian, generalized inverse Gaussian, lognormal, gamma, and exponential) across a range of thresholds as an indicator of whether the identified peaks accurately capturing the temporal structure in the EDA data (step 410). For each threshold and distribution, the processor computes a Kolmogorov-Smirnov (KS) distance after rescaling the inter-pulse intervals using the time-rescaling theorem (step 412). The time-rescaling theorem states that any point process can be rescaled to a Poisson process with rate 1 using the density of the appropriate distribution. The KS distance represents the maximum distance between the quantiles of the rescaled data and the uniform distribution, which is a simple transform of a rate 1 Poisson process done for visual simplicity.

Figure 5B:
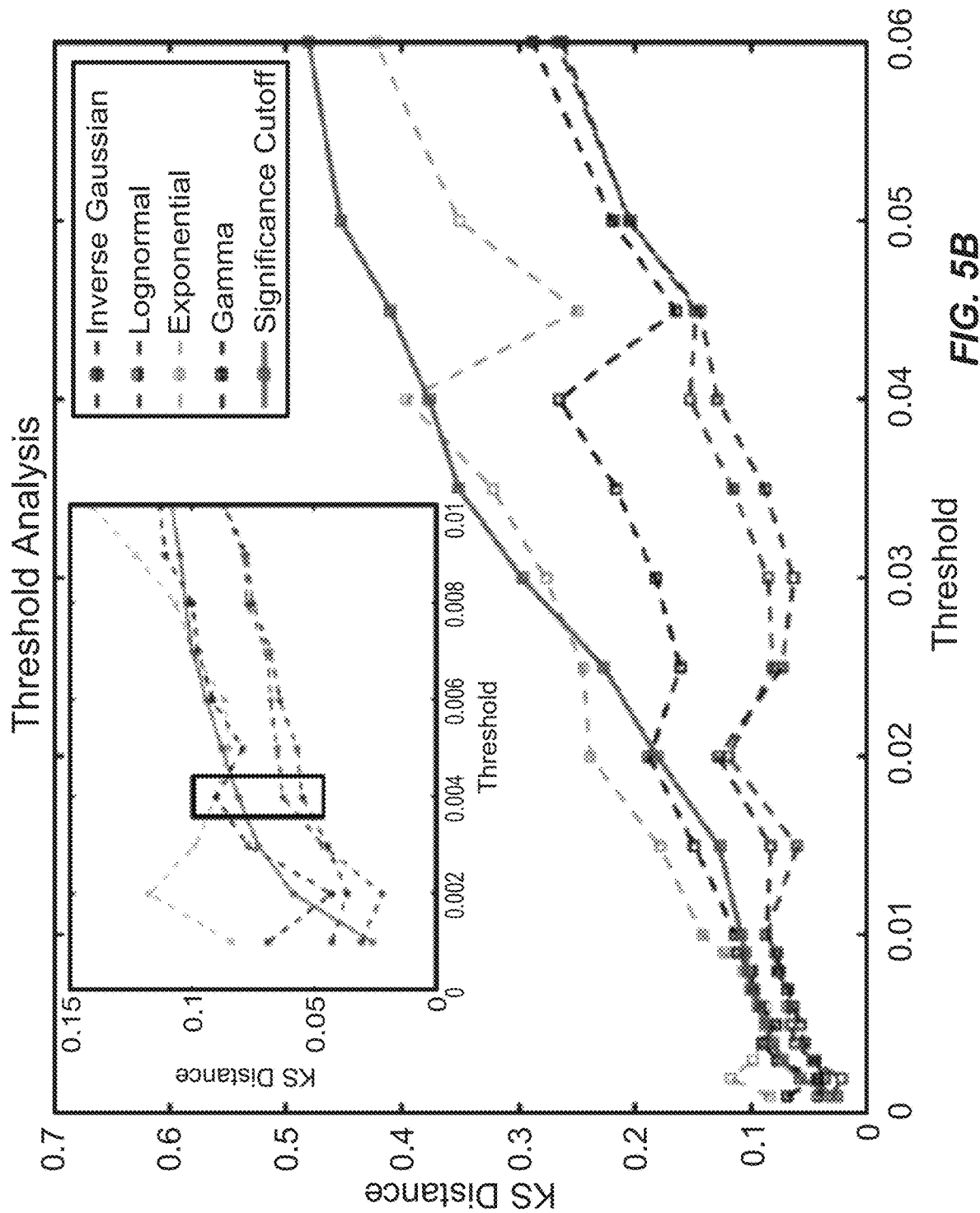
FIG. 5B illustrates a threshold analysis of the phasic EDA data in FIG. 5A showing the KS distances of different distributions at various thresholds for identifying peaks and highlighting the selected threshold. The inset plot is a zoom-in of the lower-threshold region for clarity.

FIG. 5B shows the KS distances for each distribution at each threshold along with the 95% significance cutoff given by the number of pulses at that threshold. The significance cutoff increases with increasing threshold as the number of pulses decreases. A KS distance below the significance cutoff shows that the theoretical and empirical distributions are not statistically significantly different from each other.

Figure 5C:
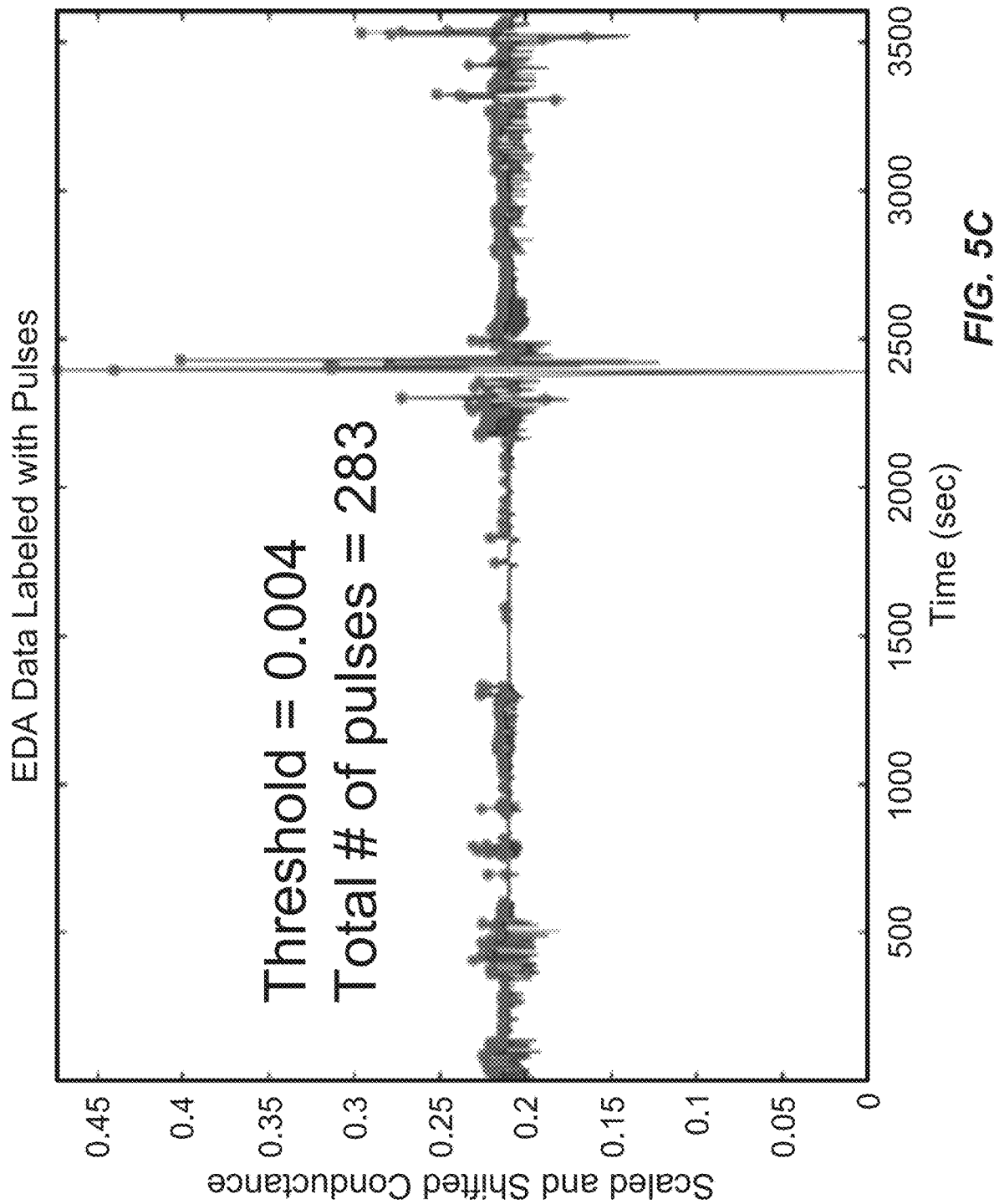
FIG. 5C shows the EDA data of FIG. 5A with identified pulses labeled at the threshold selected in FIG. 5B.

The data in FIG. 5B can be used to determine the upper and lower bounds of the appropriate threshold for peak finding (step 414). The upper bound is the point at which all tested distributions fell under the significance cutoff as a marker of having too few pulses for one hour of data. The lower bound is the point at which light or medium tailed distributions such as the gamma and especially the exponential are no longer under the significance cutoff. Within the acceptable range of thresholds, the selected threshold is the threshold at which the KS distance for the gamma and exponential distributions is as far above the significance cutoff as possible. A black box marks the final threshold in FIG. 5B. And FIG. 5C shows the pulses on the phasic EDA identified with the final threshold (step 416).

Figure 5D:
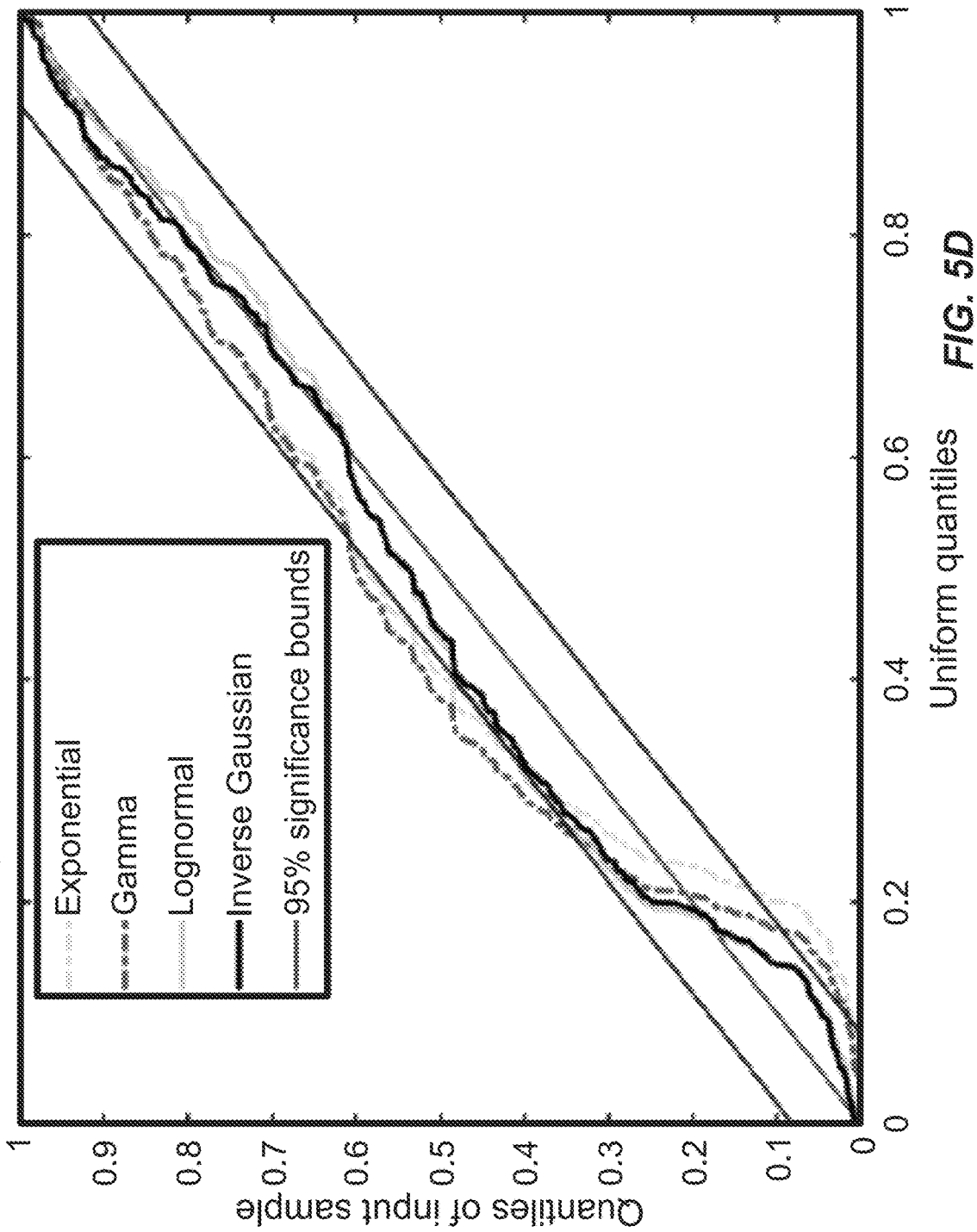
FIG. 5D shows Kolmogorov Smirnov (KS) plots showing the goodness-of-fit of all of the distributions at the threshold selected in FIG. 5B.

FIG. 5D shows a goodness-of-fit of all distributions at the final threshold with KS plots. The KS plots show the quantiles of rescaled inter-pulse intervals against the quantiles of the uniform distribution, transformed from a Poisson process with rate 1. The 95% significance bounds are also shown in FIG. 5D.

The method 400 in FIG. 4 for preprocessing and analyzing EDA data relies heavily on the properties of several distributions, namely the inverse Gaussian, lognormal, gamma, and exponential, which differ specifically in their tail behavior. The inverse Gaussian is a heavier tailed distribution at these parameter values, with a density that "falls off" at a slower rate than the exponential and gamma distributions. The lognormal distribution is also heavier tailed than the exponential and gamma distributions. The method 400 in FIG. 4 exploits these heavier tails to capture the temporal structure in EDA data without sensor noise. This increases the signal-to-noise ratio (SNR), which is a significant technological advantage over other techniques for processing EDA data.

In particular, the method 400 in FIG. 4 makes it possible to identify smaller "micropulses" in the EDA data that are traditionally excluded from analysis to accurately capture the temporal structure in EDA data. This temporal structure results in right-skewed heavy tailed distributions because there are many regions with widely spaced micropulses resulting in long inter-pulse intervals (also seen in FIG. 5C). Setting too high a prominence threshold may exclude the micropulses. On the other hand, setting too low a threshold may include 'pulse-like' activity that results from sensor noise and mask the true temporal structure of the EDA. Optimized the threshold determination by identifying where the data were fit well by the inverse Gaussian and lognormal distributions but not as well by the exponential or gamma distributions, as shown in FIG. 5B, captures micropulses and excludes sensor noise.

FIG. 5D shows the inverse Gaussian and lognormal distributions remain fully within the significance bounds, while the exponential and gamma distributions do not. The fact that the KS plots of the exponential and gamma distributions have a steeper slope and exceed the significance bounds specifically around the upper quantiles reflects their faster decrease in the tail compared to the inverse Gaussian and lognormal distributions. Both the inverse Gaussian and the lognormal distributions can be used to model RR-interval and neural inter-spike intervals. Pulse selection should be optimized using temporal structure in the EDA data because the characteristics of pulses can change drastically even for the same subject at different times. The statistical structure in the data is a direct link to the underlying physiology of the sweat gland.

Constructing a Point Process Model for EDA

Figure 6:
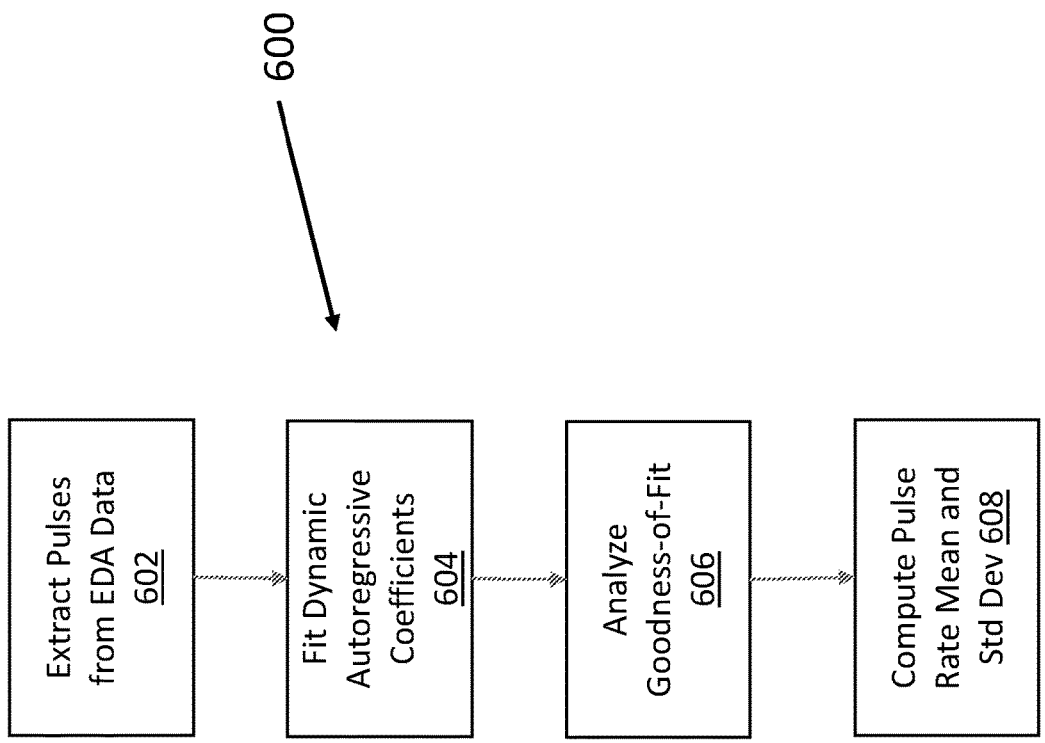
FIG. 6 illustrates a method of constructing a point process model for EDA using pre-processed EDA data.

FIG. 6 illustrates a method 600 for constructing a point process model for EDA from EDA data pre-processed using the method 400 of FIG. 4. This method 600 takes advantage of inverse Gaussian structure in the EDA data. Unlike other models, a point process model can capture autonomic dynamics of the EDA data. When used for heart rate variability, the structure of the point process model includes history dependence to account for autonomic changes that last across several heartbeats; these same autonomic dynamics likely also cause dependencies in EDA.

The first step 602 of this method 600 is to extract pulses in the EDA data (e.g., using the process 400 in FIG. 4). In step 604, the dynamic autoregressive coefficients are fit using local likelihood. The autoregressive coefficients that encode the history dependence are themselves varying in time to reflect changing autonomic dynamics. Therefore, a local likelihood estimation method can be used to fit those coefficients, where sliding windows of data are fit instead of all data at once.

Next, a goodness-of-fit analysis can be performed to assess how well the fitted model corresponds to the data (step 606). In the goodness-of-fit analysis, rescaled inter-pulse intervals can be computed using the time rescaling theorem to transform the point process model into a Poisson process with unit rate. Then, the KS-distance between the rescaled intervals and the uniform distribution can be computed and plotted. The autocorrelation of the rescaled intervals can be analyzed to verify consistency with independence. A processor (e.g., processor 106 in FIG. 1A) can determine the ideal model order (for autoregression) and window length for local likelihood estimation separately by screening through a range of values for each and minimizing the KS distance between the rescaled inter-pulse intervals and the uniform distribution. Then, using theoretical properties of the inverse Gaussian distribution, instantaneous estimates of the mean and standard deviation of the inter-pulse interval can be computed in step 608. (Because pulse rate is the inverse of inter-pulse interval, a simple change of variable allows for analogous instantaneous estimates to be computed for pulse rate.)

This point process model was validated with EDA data from two healthy volunteers between the ages of 20 and 35. All data were collected under protocol approved by the Massachusetts General Hospital (MGH) Human Research Committee. For both subjects, approximately three hours of data were recorded while using target-controlled infusion protocol. The infusion rate was increased and then decreased to achieve target propofol concentrations of 0, 1, 2, 3, 4, 5, 3.75, 2.5, 1.25, and 0 mg/kg/hr.

Figures 7A, 7B, 7C:
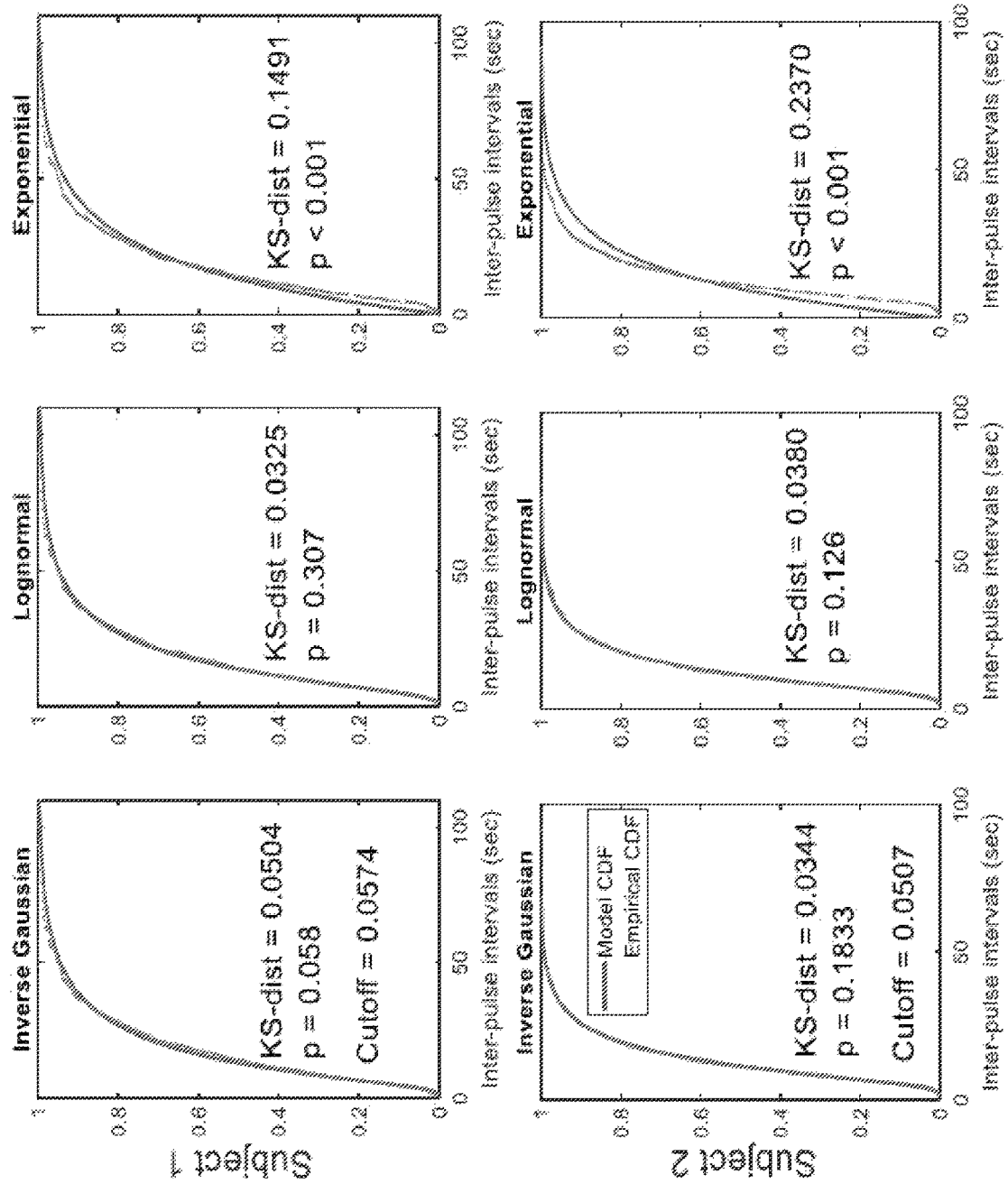
FIGS. 7A-7C are cumulative distribution function (CDF) plots for EDA data from two subjects (Subjects 1 and 2, top and bottom rows, respectively) compared to inverse Gaussian, log-normal, and exponential distributions, quantified with KS distances, significance cutoff, and p-values. N=560 pulses for Subject 1 and N=718 pulses for Subject 2.

FIGS. 7A-7C show KS plots for EDA data from two subjects (Subjects 1 and 2, top and bottom rows, respectively) compared to inverse Gaussian, log-normal, and exponential distributions, quantified with KS distances, significance cutoff, and p-values. N=560 pulses for Subject 1 and N=718 pulses for Subject 2. FIGS. 8A-8C show the final values of model order and window length, along with the goodness-of-fit analyses for both subjects. FIGS. 9A-9E show the instantaneous estimates for mean and standard deviation of pulse rate returned by the model for both subjects. The vertical lines indicate changing dosage of propofol, which is also shown in an infusion vs. time plot for reference.

FIGS. 7A-9E reveal several insights. Based on FIGS. 7A-7C, for both subjects, the models fit well to the lognormal and inverse Gaussian distributions, evidenced by the KS distances being well below the significance cut-offs, but not to the exponential distribution. This indicates that there is clear structure in the inter-pulse interval data which can be captured using just two parameters. This also suggests that the pulses may themselves be meaningful without recovering the neural input as with deconvolution methods.

FIGS. 8A-8C shows that for both subjects, the history-dependent inverse Gaussian model fits well, evidenced by the cumulative distribution function (CDF) of the rescaled intervals remaining fully within confidence bounds and the lack of significant correlation in the rescaled intervals for lags of up to 60. For both subjects, the best model order was 1 and the optimal window for local likelihood estimation was roughly 1000 seconds.

FIGS. 9A-9E show that there are instantaneous dynamics under sedation for both subjects. There are a number of similarities in dynamics across both subjects. First, each increase in propofol concentration for the first five epochs marks transient increases in mean and standard deviation of pulse rate for both subjects, possibly due to reflex increase in sympathetic tone in response to vasodilation caused by propofol. For Subject 1, these increases are visible for all five increases in propofol concentration, with some delay after the second and third. For Subject 2, the increases are most visible for the first three increases in propofol concentration and subtler for the last two. Later, when the concentration of propofol starts decreasing at the sixth epoch, the variation in pulse rate (standard deviation) increases compared to deeper sedation. This is most visible after 7500 seconds for Subject 1 and after 7000 seconds for Subject 2. These dynamics reflect instantaneous autonomic dynamics not discernible using current models for EDA and warrant further exploration on a larger set of subjects.

There is clear statistical structure in the EDA data from the two subjects, including in smaller pulses that are usually disregarded. Furthermore, this structure can be described using a low-dimensional point process model to track the instantaneous dynamics of sympathetic tone at rest and with intervention. This EDA point process model can be used to characterize how sympathetic dynamics change in different physiological and pathological conditions as explained below.

Determining a Point Process Model for Heart Rate Variability (HRV)

Figure 15:
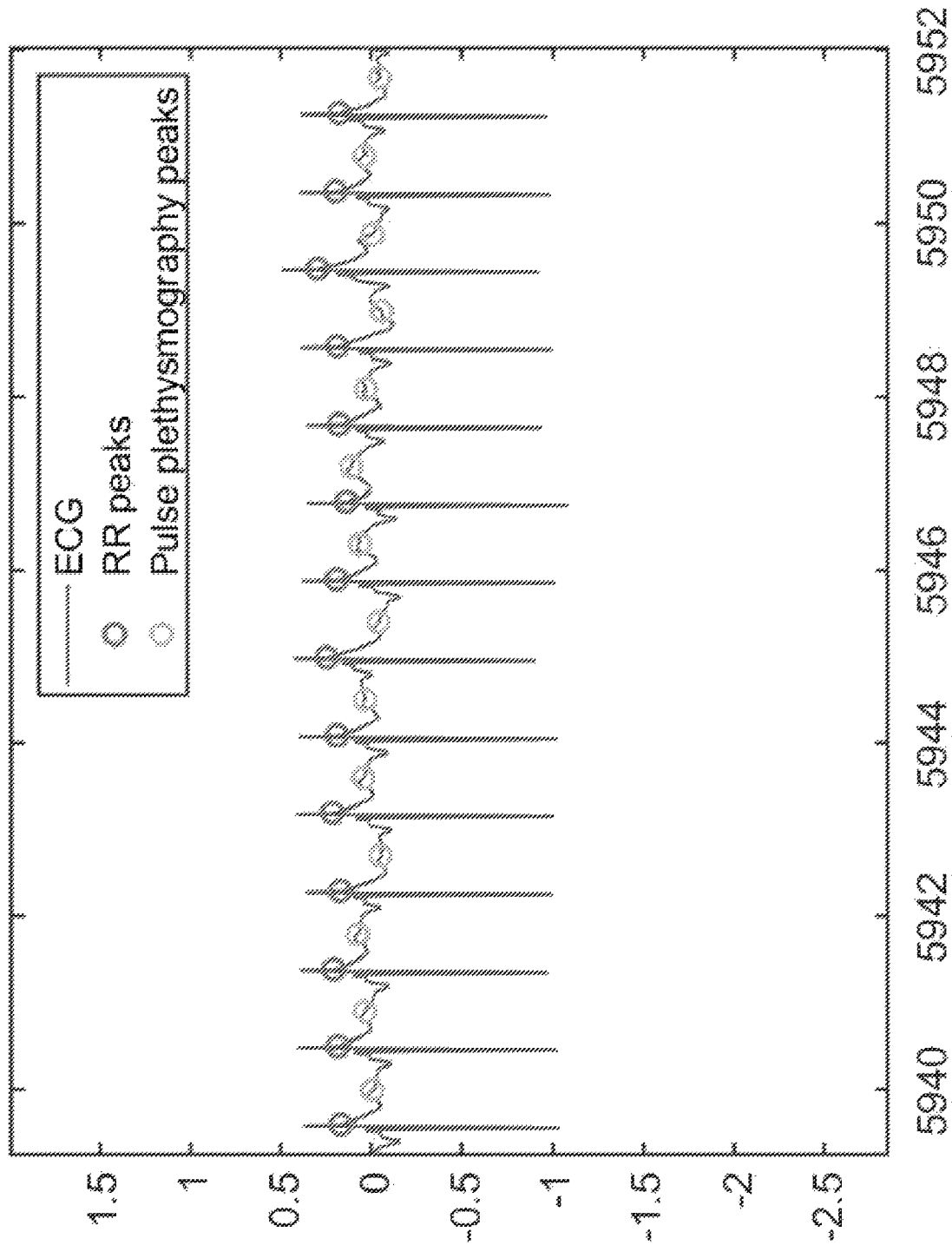
FIG. 15 shows EEG (HRV) data with RR peaks and associated peaks in the corresponding pulse plethysmogram signal marked by dark and light circles, respectively.

A point process model can also be used to assess HRV using the process in FIG. 6, with R peaks substituting for GSR peaks and different model orders and window lengths when screening for possible threshold values. (FIG. 15 shows EEG (HRV) data with RR peaks and associated peaks in the corresponding pulse plethysmogram signal marked by dark and light circles, respectively.) Assessing HRV with a point process model offers several advantages, including: (a) a point process model overcomes stationarity requirements of standard HRV analysis; (b) a point process model is physiologically justified, unlike other methods of preprocessing and filtering R-R interval series; (c) point process models include goodness-of-fit analyses to assess accuracy of heartbeat stochastic structure; (d) point process instantaneous HRV indices can be computed in parallel from a single statistical framework in continuous time at any time resolution; and (e) analogs to standard HRV measures (e.g. standard deviation of the RR interval (SDNN) in the time domain and high frequency (HF) (4-15 Hz)/low frequency (LF) (1-4 Hz)) can be obtained by averaging instantaneous point process indices. These results suggest that measures derived from point process models give a more accurate result.

The point process model for HRV treats the RR interval as a history-dependent inverse Gaussian process with a density function given by:

$$f(t \mid H_{u_k}, \theta) = \left[\frac{\theta_{p+1}}{2\pi(t-u_k)^3}\right]^{\frac{1}{2}} \exp\left\{-\frac{1}{2}\frac{\theta_{p+1}[t-u_k-\mu(H_{u_k}, \theta)]^2}{\mu(H_{u_k}, \theta)^2(t-u_k)}\right\}$$

where $H_{u_k} = (u_k, w_k, w_{k-1}, \ldots, w_{k-p+1})$ is the history up to the most recent R complex at time $u_k$, $w_k = u_k - u_{k-1}$ is the kth RR interval, and $\mu(H_{u_k}, \theta) = \theta_o + \Sigma_{j=1}^{p} \theta_j w_{k-j+1}$ is the mean RR interval at time $u_k$.

The formulas for heart rate (HR) and HRV follow directly from this model through a transformation of variable. HR is a reciprocal transformation of this probability density. The processor can compute instantaneous HR estimates of these quantities and several others, such as linear and nonlinear sympathovagal indices of HRV, baroreflex, and respiratory sinus arrhythmia. These methods have been successfully applied during induction and emergence from general anesthesia, further identifying measures of complexity and nonlinearity associated with loss of consciousness. These results demonstrate that the point process framework is suitable for application to ECG of patients under general anesthesia, providing accurate characterization of autonomic nervous system (ANS) state at different stages, and tracking ANS dynamics at high time-resolution.

Using EDA Pulse Amplitude Information

Pulsatile EDA can be modeled as an integrate-and-fire process. When the sudomotor nerve increases firing, sweat accumulates and rises up in the sweat gland until it reaches the surface of the skin, where it is measurable in the form of a transient increase in the electrical conductance of the skin (i.e., a GSR). The continuous measurement of the electrical conductance of the skin is EDA, and GSRs appear as discrete pulse-like phenomena as explained in greater detail above. The distribution of inter-pulse intervals follows an inverse Gaussian model across subjects and experimental conditions, again, as explained in greater detail above. Showing that the temporal information in EDA can be summarized in a two-parameter model is a level of dimensionality reduction previously unseen for EDA. In addition, this enables the application of a variety of point process techniques to EDA data to extract information about dynamic sympathetic nervous system activity with relatively low computational complexity while ensuring physiologic relevance.

However, temporal information is not the only information in EDA data. Each pulse, besides occurring at a discrete point in time, also has an amplitude. The same integrate-and-fire model postulated for sweat glands can be expanded to account for the pulse amplitudes, which are proportional to the excess volume of sweat produced compared to what would be required to reach the surface of the skin. Thus, amplitudes of GSRs can be incorporated into the EDA point process model described above using the amplitudes of the pulses identified in the EDA data. More specifically, temporal and amplitude information from the EDA data can be modeled using two separate point process models or combined into one point process model where the events, instead of being binary, have an amplitude or mark, and this amplitude has its own probability model.

For example, the amplitudes can be modeled as the difference of two inverse Gaussians for each pulse: a first inverse Gaussian that represents the time to produce just enough sweat to rise to the surface of the skin and a second inverse Gaussian that represents the time to produce the actual amount of sweat produced.

Fitting a different set of two inverse Gaussians to each pulse can be computationally intensive and under-constrained. To alleviate this computational complexity, this model of EDA pulse amplitude can be simplified in at least four ways. First, the entire set of pulse amplitudes can be fit to a single difference of inverse Gaussians using the method of moments. Fitted parameter values for subject test data indicate that the second inverse Gaussian actually approaches a very narrow Gaussian. Therefore, the second simplification is a single difference of an inverse Gaussian and a Gaussian. Results from these simplifications suggest that the second very narrow distribution could be simplified to single point shift. This suggests a third simplification: fitting EDA pulse data to a three-parameter inverse Gaussian model using the method of moments, with the third parameter being the location shift. Fourth, the entire set of pulse amplitudes from each subject can be fit to a single simple inverse Gaussian using maximum likelihood estimates of the parameters.

Preliminary results indicate that all simplifications are reasonable models for the data and outperform other classes of distributions overall; however, each prioritizes different aspects of the fit. The first two simplifications generally better fit the right tail of the distribution by sacrificing some of the fit near the mode of the distribution as compared to the simple inverse Gaussian. The three-parameter model seems to balance the fit of both inverse Gaussians reasonably well.

Constructing a Multimodal Model from EDA and HRV Point Process Models

As discussed above, a state space framework to estimate the underlying a person's SDAS (e.g., nociceptive state under anesthesia) can be constructed based on point process models for HRV and EDA. Experimental data and analysis shows that the SDAS decreases (i.e., there is less sympathetic activity) with deep, slow breathing and increases (i.e., these is more sympathetic activity) with increasing breathing rate. The following results show that a unimodal model based solely on LF- and HF-derived observations estimates the highest SDAS at the slowest stage of breathing due to the confound of the breathing rate. On the other hand, a multimodal model correctly estimates a low SDAS at the slowest breathing stage which then increases with breathing rate. These results suggest that a multimodal estimation of SDAS is a more accurate and robust representation of the underlying information, especially in situations with possible confounds.

To show this, data was collected from five healthy volunteers between the ages of 22 and 34 with approval from the Massachusetts Institute of Technology Institutional Review Board. The subjects were asked to perform a paced breathing task in which they had to breathe at each of three rates for three minutes each. The breathing rate were 0.1 Hz (6 breaths per minute), then 0.2 Hz (12 breaths per minute), and finally 0.3 Hz (18 breaths per minute). Continuous ECG, respiration (using a deflection sensor around the torso), and EDA data were collected throughout the paced breathing task. Three of the subjects had a two-minute baseline period before the start of the task.

Then, a series of features from the collected data were computed. Using a point process HRV model (discussed above), instantaneous estimates of mean and standard deviation of HR as well as frequency domain measures of heart rate variability such as LF/HF and HFu were computed.

The EDA data was filtered into a slow-moving tonic or baseline component and a pulsatile phasic component from which pulses were extracted. The details of EDA processing are discussed above with respect to FIGS. 4 and 6.

estimations for two different subjects. (The subject in FIGS. 11A-11E had an additional baseline period before the start of the task.) Looking at the respiration data in FIGS. 10A and 11A, the respirations clearly delineate the three stages of the task, including the baseline beforehand for the second subject. Vertical lines in FIGS. 10E and 11E separate the three breathing stages of the task.

Figures 10A, 10B, 10C, 10D:
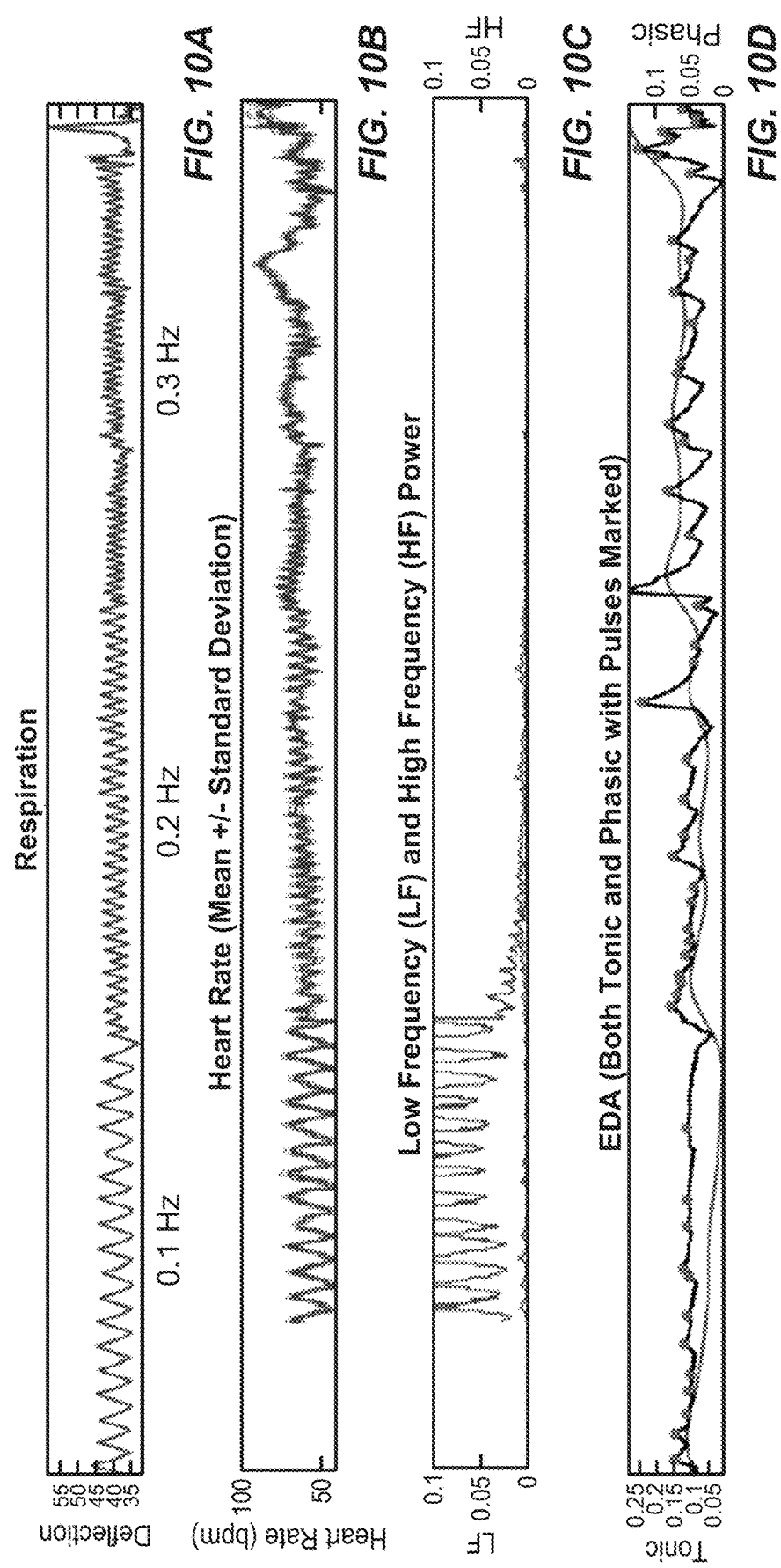
FIGS. 10A-10E illustrates a third subject's paced breathing task results, showing respirations (FIG. 10A), instantaneous heart rate plus and minus the standard deviation (FIG. 10B), instantaneous estimates of low-frequency (LF; left axis) and high-frequency (HF; right axis) power (FIG. 10C), tonic (left axis) and phasic (right axis) EDA activity with labeled pulses (FIG. 10D), and sympathetic driven arousal state (SDAS) estimates in a state space model with multimodal versus unimodal observations (FIG. 10E).

FIGS. 10B and 11B shows that while the mean heart rate oscillates noticeably due to respiratory sinus arrhythmia (RSA), there is no clear trend in terms of increasing or decreasing heart rate across the three stages of the task. This also holds true for the standard deviation of the heart rate. The RSA is most pronounced in the slowest stage of breathing.

Because the breathing frequency of the first stage of the task (0.1 Hz) falls squarely in the range of LF, it is strongly affected by the RSA and mimics the same oscillatory pattern with high amplitude during the first stage of the task as shown in FIGS. 10C and 11C. While HF also seems to have some oscillations throughout, they are much smaller in amplitude. Finally, there seems to be no consistent trend in either the tonic or phasic EDA across the different stages of the task as shown in FIGS. 10D and 11D.

TABLE 1

| Observation | Details of Computation |
| --- | --- |
| Mean heart rate | Point process HRV model, averaged for each window |
| Standard deviation of heart rate | Point process HRV model, averaged for each window |
| LF/HF | Point process HRV model, averaged for each window |
| HFu | HFu = HF/(LF + HF) Point process HRV model averaged for each window |
| Tonic EDA | Low pass filter on EDA data averaged for each window |
| Phasic EDA | Pulses extracted from phasic EDA. In each window, either 0 (if no pulse) or pulse amplitude (if there is a pulse) |

The mean of each feature in non-overlapping 0.5 second windows was taken as observations for a state space model. For phasic EDA, observations were either zero or a pulse amplitude within each window. The six observation time series are summarized in Table 1.

A linear Gaussian state space approach was applied to estimate each subject's underlying SDAS. This framework models SDAS evolution over time as an autoregressive process, where the observations depend only on the underlying state at each time point. The state evolution and observation equations of the multimodal model are below.

State Evolution Equation:

$$x_k = A + Bx_{k-1} + \varepsilon_x, \varepsilon_x \sim N(0,Q)$$

Observation Equation:

$$Y_k = E + Fx_k + \varepsilon_y, \varepsilon_y \sim N(O,R)$$

The unimodal and multimodal models were tested, one with all six observation time series, and one with only LF/HF and HFu as observations. Expectation maximization was used to simultaneously estimate the underlying state over time and the parameters of the model (A,B,E,F,Q,R). Expectation maximization uses a forward filter and backward smoother to estimate the underlying state and maximum likelihood estimation of the model parameters. Finally, the estimates of the underlying state evolution over time from both models were compared.

Estimating SDAS with a Multimodal Model

Figure 10E:
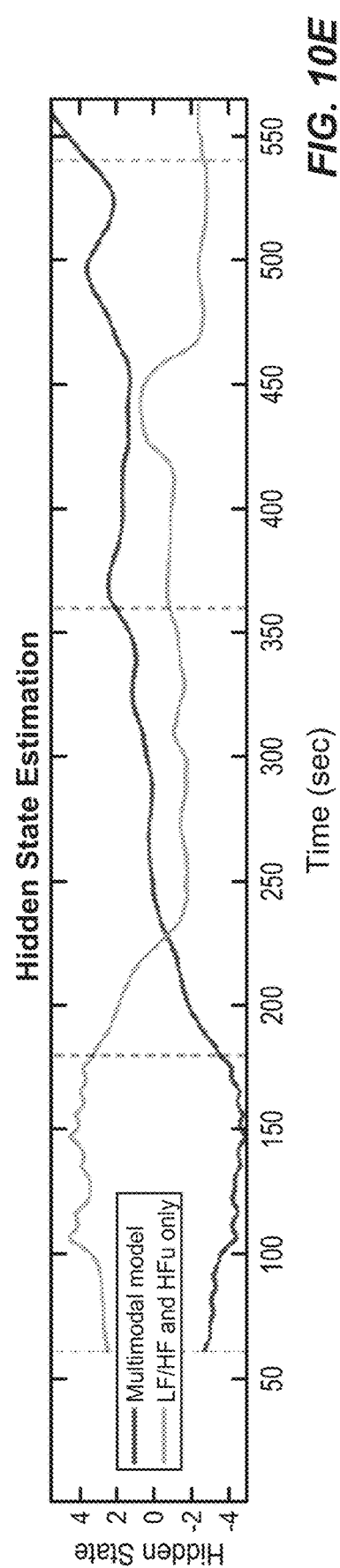
Figure 11E:
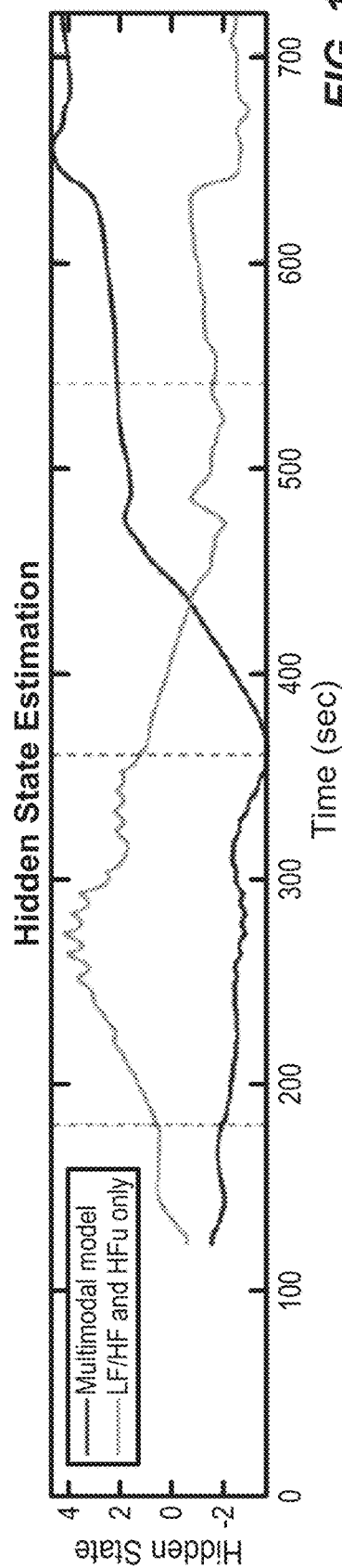
Figure 12:
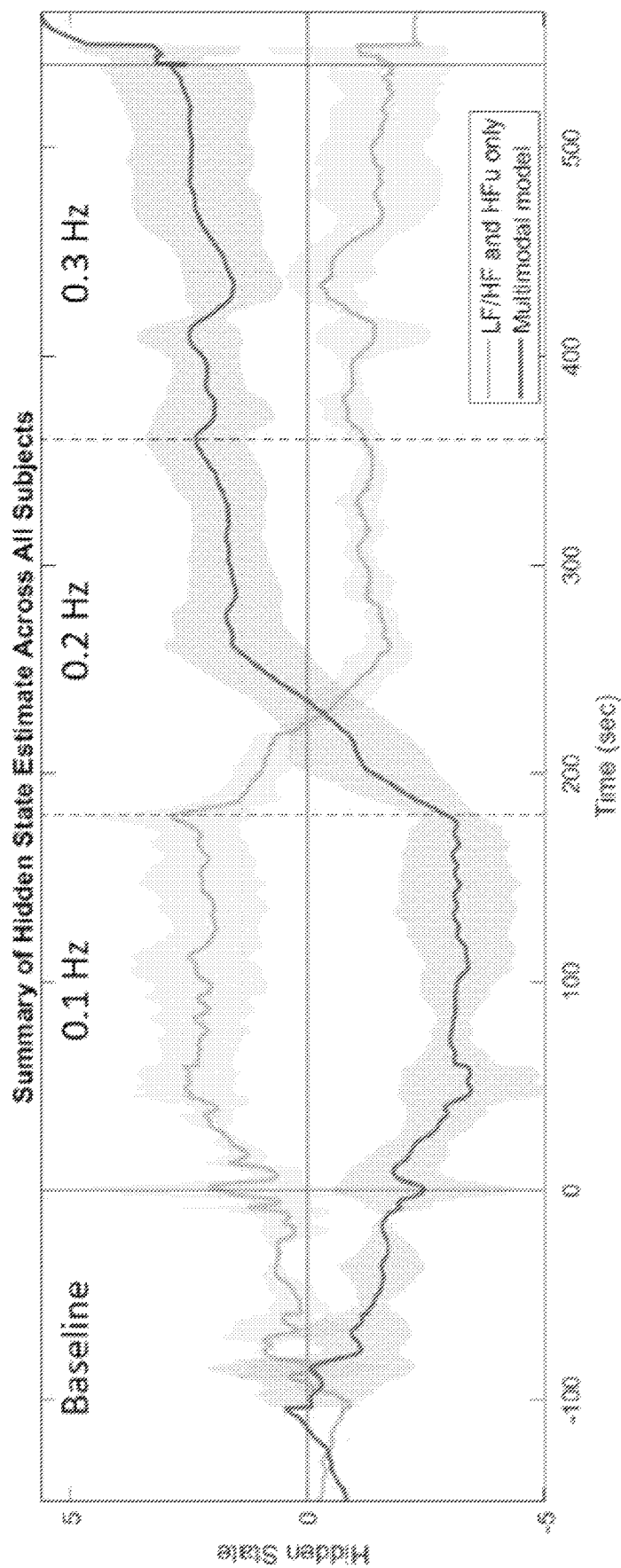
FIG. 12 illustrates SDAS estimates averaged across five subjects.

FIGS. 10A-10E and 11A-11E show respiration, mean heart rate, HF and LF power, EDA, and hidden (SDAS) state FIGS. 10E, 11E, and 12, which shows SDAS estimates across subjects, indicate that unimodal and multimodal models consistently give very different estimates of the SDAS throughout the paced breathing task. In FIG. 12, the start and end of the task are at 0 and 540 seconds respectively and the stages are separated with dashed vertical lines.

The unimodal model, which uses only LF and HF derived features as observations, estimates the SDAS of the first stage of the task to be high, higher than that of baseline even. This initial overestimate, which appears to be influenced strongly by the effect of RSA on LF, is also much higher than the SDAS estimate in subsequent stages of the task. In contrast, the multimodal model estimates a very low SDAS during the first stage of the task, decreasing from baseline. Then the SDAS estimate increases through the second and third stages of the task, with most of the increase happening in the second stage.

The multimodal model is in better agreement with known physiology associated with deep, slow breathing. Slow, deep breathing is a core component of many stress relief practices, including yoga and meditation, as well as a recommended therapeutic strategy for anxiety or panic attacks. In all of these cases, the goal is to drive down sympathetic activation. In addition, studies have shown that guided breathing exercises increase vagal activity and decrease blood pressure and peripherical sympathetic nerve activity.

The multimodal model provides a more accurate estimate of the true SDAS as being low during the first stage of the task, especially compared to normal baseline level of activity. The unimodal model not only overestimates the SDAS during the first stage of the task, it biases the SDAS for the other two stages of the task due to the frequency-dependent buffering of RSA.

The multimodal model can overcome influence of RSA on LF at the slowest stage of breathing based on combined information from the other observations and even in the absence of a clear trend in any of them. This supports the use of multimodal signals to inform SDAS estimation, especially when there is no information about breathing rate.

Analyzing Transitions in Anesthesia with a Multimodal Model

The multimodal model of SDAS is particularly useful for analyzing transitions in an unconscious subject, e.g., a subject under anesthesia. In particular, a multimodal model of autonomic state can distinguish the dynamics of transitioning into propofol sedation from baseline (induction) from the dynamic of transitioning out (emergence). Including a history of previous dynamics improves the multimodal model's performance. And the multimodal model can distinguish a "baseline" after propofol sedation distinguishable from the baseline before propofol sedation.

A goal of this study was to build one possible implementation of autonomic state (using logistic regression) and understand its relationship with drug concentration. EEG is the most informative marker to detect level of consciousness, but autonomic state is a separate entity that must be monitored and controlled separately in general anesthesia. The two may interact since the same drugs often have some effect on both. Comparing baselines before and after sedation establishes the distinctness of autonomic state from level of consciousness.

Unlike unimodal models based solely on HRV, a multimodal model can provide a view of dynamics instead of static snapshots. Moreover, HRV-based studies have not found enough evidence to separate the autonomic state of baseline from anesthesia, even though the mechanisms of many anesthetics are known to include hemodynamic and other autonomic effects. This may be due to the use of physiologically inaccurate methods based on time-averaging to compute HRV indices.

The multimodal model was validated with data from eleven healthy volunteers, collected under protocol approved by the Massachusetts General Hospital (MGH) Human Research Committee were analyzed. For all subjects, approximately three hours of data were recorded while using target-controlled infusion protocol. The infusion rate was increased and then decreased in a total of ten stages of roughly equal lengths to achieve target propofol concentrations of 0, 1, 2, 3, 4, 5, 3.75, 2.5, 1.25, and 0 mg/kg/hr in that order. Continuous electrocardiogram (ECG), skin conductance (EDA), and blood pressure (BP) were collected.

Table 2 lists twelve different autonomic indices with their descriptions. HRV indices were computed from ECG using point process methods that yield instantaneous estimates for mean and standard deviation of RR interval and heart rate as well as frequency domain metrics. Analogous methods were used to arrive at instantaneous estimates of the mean and standard deviation of the pulse rate in EDA, based on discovery of similar point process structure. Finally, systolic and diastolic blood pressures were extracted from the continuous BP. All twelve indices were then concatenated into autonomic state vectors for each 30-second window by computing the median value of each index within each window. The 30-second windows were also labeled by stage (propofol concentration).

TABLE 2

| Index | Modality | Description |
| --- | --- | --- |
| muRR | ECG | Mean RR interval |
| sigmaRR | ECG | Standard deviation of RR interval |
| muHR | ECG | Mean heart rate |
| SigmaHR | ECG | Standard deviation of heart rate |
| LF | ECG | Low freq. power, absolute (0.04-0.15 Hz) |
| HF | ECG | High freq. power, absolute (0.15-0.4 Hz) |
| LF/HF | ECG | Ratio of LF/HF (sympathovagal balance) |
| Total power | ECG | Total autonomic tone |
| muPR | EDA | Mean pulse rate in EDA |
| sigmaPR | EDA | Standard deviation of pulse rate in EDA |
| SBP | BP | Systolic blood pressure |
| DBP | BP | Diastolic blood pressure |

Table 3 shows whether the dynamics of transitioning into propofol sedation from baseline (induction) can be separated from transitioning out (emergence) purely based on multimodal autonomic state, whether including history of previous dynamics improves performance, and whether the "baseline" after propofol sedation is distinguishable in terms of autonomics from the baseline before propofol sedation. Table 4 shows which covariates were included in the final validated model for each question with the signs of the coefficients.

To assess the transition dynamics, logistic regression was performed by grouping the first six stages as induction (increasing propofol) and the last four as emergence (decreasing propofol). The autonomic state vectors were the covariates and a prediction was computed for each 30-second window. Within-subject normalization preceded concatenation across subjects. Three subjects were left out of this part of the study because of ambiguity in annotation of the stages of sedation. LASSO (i.e., L1 regularization) was used to prune covariates; Akaike information criterion (AIC) was used for model selection. Ten-fold cross-validation was performed and Area Under Curve (AUC) computed. It was also examined which covariates were included in the best performing model.

To assess whether history improves, performance, the same analysis was performed except that for each time-window, the four previous time windows' autonomic state vectors were also included as covariates. Since LASSO was once again used, only history that was informative for each index was included in the final model.

And to assess differences in baseline, logistic regression was performed, but only including the first and last stages of the experiment for each subject (both with propofol concentration of 0). All 11 subjects were included. No time lagged columns were included since we assume stationary dynamics during baseline.

TABLE 3

| Task | # Subjects, # Windows | Training vs Validation | AUC |
| --- | --- | --- | --- |
| Induction v | 8, | Training | 0.705 |
| Emergence | 2905 | Validation | 0.706 |
| Induction v | 8, | Training | 0.765 |
| Emergence + History | 2905 | Validation | 0.711 |
| Baseline before v | 11, | Training | 0.826 |
| Baseline after | 1653 | Validation | 0.825 |

One of the subjects had a very long baseline period of almost 4 hours, without a clear starting point annotated for the experiment. That subject was removed, and the other baselines were standardized at the beginning to 20 minutes in length. Including history in both models enables assessment of any improvement in performance. The results are below:

TABLE 4

| Task | # Subjects, # Windows | Training vs Validation | AUC |
| --- | --- | --- | --- |
| Induction v Emergence | 8, 2905 | Training Validation | 0.730 0.722 |
| Baseline before v Baseline after | 11, 1653 | Training Validation | 0.971 0.960 |

TABLE 5

| Covariate | Induction v Emergence | Induction v Emergence + History | Baseline before v Baseline after |
| --- | --- | --- | --- |
| muRR | | | |
| sigmaRR | + | | + |
| muHR | + | + | -- |
| SigmaHR | -- | + | + |
| LF | + | + | -- |
| HF | -- | -- | -- |
| LF/HF | + | + | + |
| Total power | -- | -- | |
| muPR | | | + |
| sigmaPR | + | + | -- |
| SBP | + | | -- |
| DBP | | | + |

A simpler version of Table 5 condensed by modality is below.

| Covariate | Emergence compared to Induction | Baseline after compared to baseline before |
| --- | --- | --- |
| Heart rate variability | -- | + |
| Sympathovagal balance (from HRV) | More sympathetic | More sympathetic |
| Electrodermal Activity | -- | + |
| Blood pressure | + | -- |

Table 6 The results in Tables 3 and 4 show that induction from emergence can be distinguished purely based on multimodal autonomic state (AUC>0.70 for training and validation). Including history increases performance, but also contributes to potential overfitting at the training stage. Autonomic state can be used to distinguish baseline before propofol sedation from baseline after, indicating that the concept of "returning to baseline" is perhaps inaccurate in terms of autonomics. Together, these results show that using physiologically accurate models and a multimodal description of autonomic state can capture the dynamics associated with changing propofol concentration. Existing studies that employed time-averaging methods, purely HRV-based analyses, or "snapshot" analyses could not capture these dynamics.

Covariates from all three modalities are informative in answering one or more of the questions. Four covariates—muHR, HF, LF/HF, and sigmaPR—are in all three final models. HF is a marker of parasympathetic tone, and LF/HF of sympathovagal balance, suggesting that the balance between sympathetic and parasympathetic activity is a key aspect of autonomic state changes during anesthesia.

These results suggest that anesthesia is characterized by changing dynamics not only in the brain, but also in the autonomic nervous system, which regulates the entire body. Since autonomic state is inextricably linked to homeostatic, pain-related, and other regulatory functions of the body, these underlying autonomic state dynamics can help explain negative side effects of anesthesia, such as postoperative delirium, pain, and hemodynamic instability. This establishes the feasibility of defining an autonomic state that increases markedly in the case of nociception. For a sedated patient, the goal of the sedation would be to keep this autonomic state steady and low.

Detecting Loss and Regain of Consciousness with a Multimodal Model

General anesthesia is a drug-induced, reversible state characterized by antinociception, unconsciousness, amnesia, and immobility, all while maintaining physiologic stability. Traditionally, behavioral markers such as loss of response to auditory cues have been used to discern the moment of loss of consciousness (LOC) and regain of consciousness (ROC) during anesthesia. However, drugs given for anesthesia also cause noticeable changes to the autonomic nervous system with different signatures depending on the drug class and mechanism of action. Yet it remains unclear how these autonomic changes are correlated in time specifically with the exact moments of LOC and ROC.

For example, propofol, a commonly used hypnotic for inducing and maintaining unconsciousness, also causes vasodilation, which drops the blood pressure. In addition, anesthetics 'dry out' sweat glands, leading to marked decrease in spontaneous EDA and an increase in threshold for stimulated EDA. This could cause the threshold for the intensity of the nociceptive/sympathetic stimulus for increasing EDA to increase However, the dynamics of these effects in relation to the exact moment at which a person loses consciousness (loses behavioral response) from deep propofol sedation is not known.

One goal, rather than detecting loss and recovery of consciousness, which can be done with EEG, is to understand how autonomic changes relate to behavioral changes that we use to track consciousness in time. With such understanding, more precise and robust methods for tracking different components of general anesthesia can be developed. Autonomics are not directly measuring consciousness, but they are also affected by the same drugs. The hypothesis was that perhaps there are detectable autonomic changes around the same time as the behavioral changes of loss of consciousness. This also served as another instantiation of an 'autonomic state'.

As indicated above, existing studies attempting to analyze changes in consciousness in terms of autonomic markers have looked at stages of sedation in disjoint segments, rather than continuous time, and generally only using heartrate variability indices. In addition, they have not looked specifically at the time periods immediately around LOC and ROC.

In this section, the time periods immediately preceding and following LOC and ROC for healthy volunteers under propofol sedation using multimodal autonomic indices were analyzed. How the features seem to change were also analyzed in order to improve understanding of propofol anesthesia and its autonomic effects. HRV, BP, and EDA were used to assess LOC and ROC. While it is known that propofol decreases blood pressure, the nuances of how it affects HRV and EDA variability are not understood, especially around LOC and ROC. To begin with, it was hypothesized that LOC and ROC correlate with marked autonomic changes, such that before and after LOC (or ROC) can be distinguished with a trained model.

Data from eleven healthy volunteers, collected under protocol approved by the Massachusetts General Hospital (MGH) Human Research Committee were analyzed. For all subjects, approximately 3 hours of data were recorded while using target-controlled infusion protocol. The infusion rate was increased and then decreased in a total of ten stages of roughly equal lengths to achieve target propofol concentrations of: 0 mg/kg/hr, 1, 2, 3, 4, 5, 3.75, 2.5, 1.25, 0.

Continuous ECG, EDA, and BP were collected from each subject. LOC and ROC times were annotated based on lack of response to a button-pressing task. There were other interventions included in the study for patient safety, such as administering phenylephrine (a pressor). Two subjects were left out of this part of the study because of lack of or ambiguity in annotation of LOC and ROC. All data were analyzed using Matlab R2019a.

The process followed for ROC was analogous to that for LOC. First, the time before and after annotated LOC for each of the nine subjects were extracted, where the time t was either 10, 15, or 20 minutes. Then, for that segment, twelve autonomic indices were computed, listed in Table 2 (above) with descriptions. HRV indices were computed from ECG using point process methods that yield instantaneous estimates for mean and standard deviation of RR interval and heart rate as well as frequency domain metrics. Analogous methods were used to arrive at instantaneous estimates of the mean and standard deviation of the pulse rate in EDA, based on discovery of similar point process structure. Finally, systolic and diastolic blood pressures were extracted from the continuous BP. All twelve indices were then concatenated into autonomic state vectors for each w-second window by computing the mean value of each index within each window, where w was 10, 15, or 30. The w-second windows were labeled as before or after LOC (or ROC).

Then logistic regression models were built, with LASSO regularization for feature pruning and using leave-one-subject-out cross-validation. Predictions were computed for each subject, and AUC was used as the measure of overall predictive performance. The data were normalized within each subject before being combined, and the coefficients from the nine cross-validated models were averaged to see overall changes in each feature. Additionally, models that allowed for lagged windows to be incorporated as additional features were tested, which accounts for a longer-range history of up to h seconds, where h was either 60 or 120. For the best model for each task (LOC and ROC), the predictions were plotted for each subject and examined the signs of the averaged coefficients to compare which features change in which direction with LOC and ROC.

Figure 13:
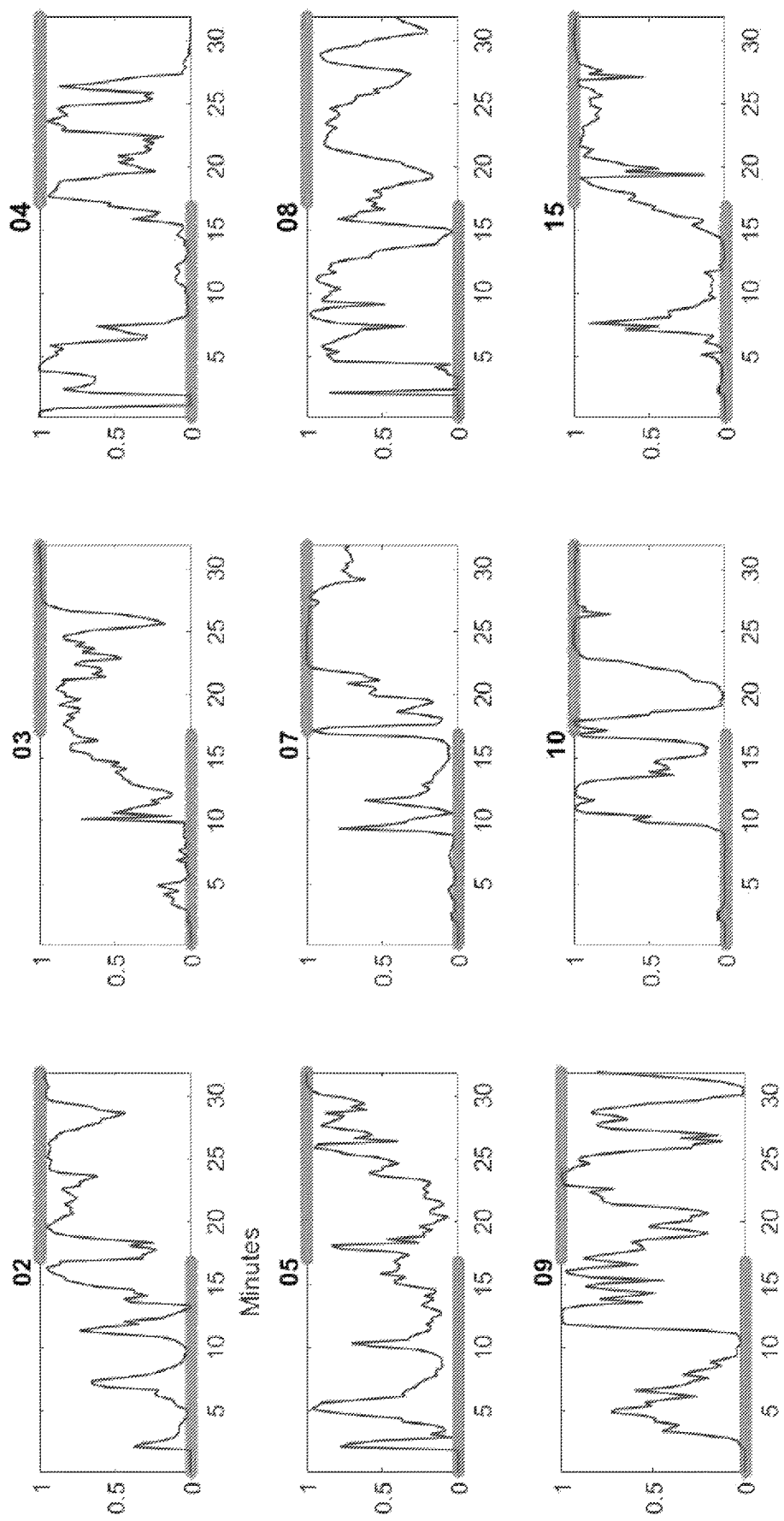
FIG. 13 illustrates loss of consciousness (LOC) predictions the best-performing multi-modal model with ground truth indicated by overlapping asterisks (0 indicates consciousness and 1 indicates unconsciousness).
Figure 14:
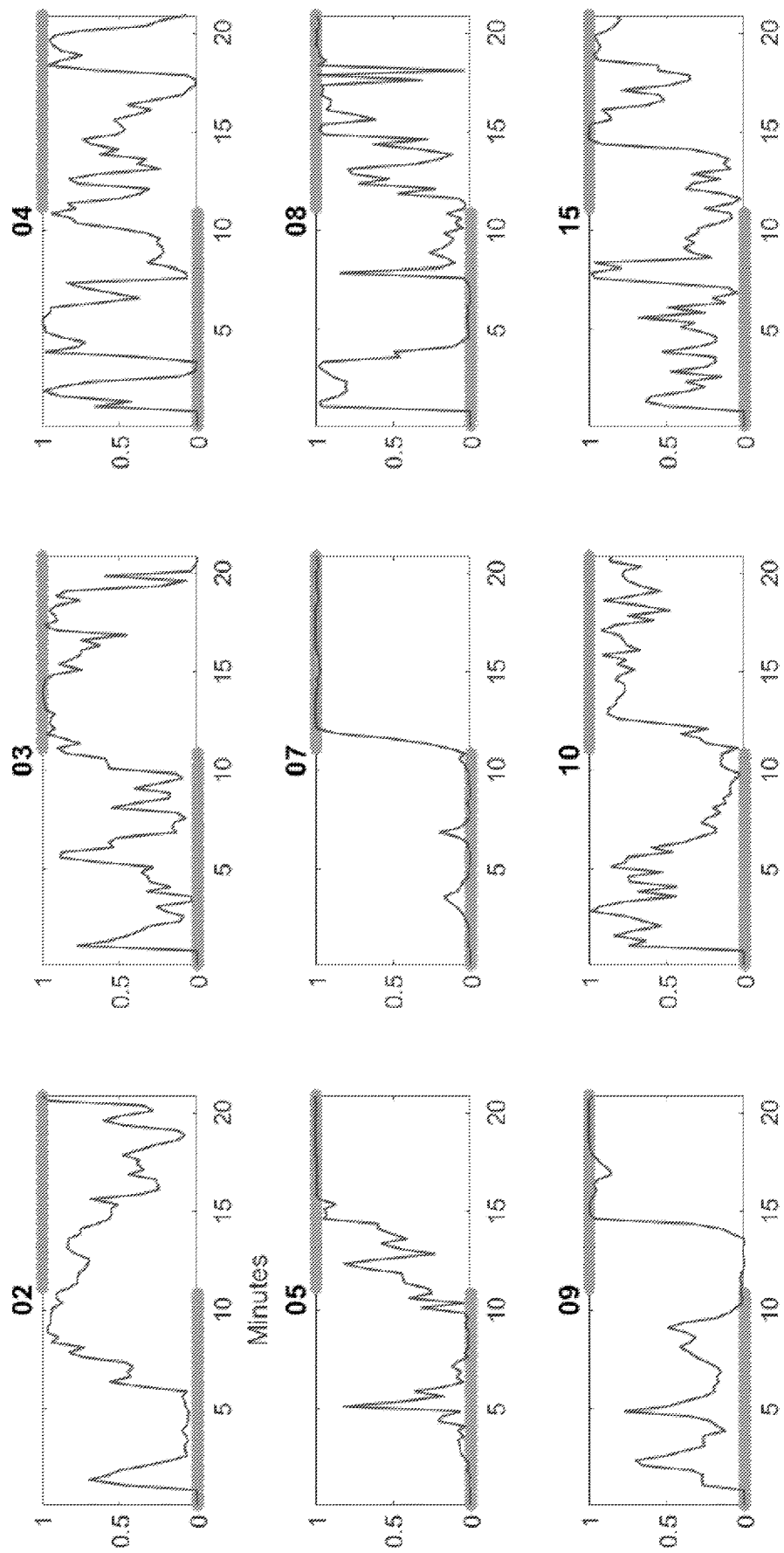
FIG. 14 illustrates regain of consciousness (ROC) predictions for the best-performing multi-modal model with ground truth indicated by overlapping asterisks (0 indicates unconsciousness and 1 indicates consciousness).

Tables 5 and 6 summarize the results for testing a variety of values of t, w, and h for LOC and ROC respectively, with the best model for each task in bold. FIGS. 13 and 14 show the predictions by subject for the best models for LOC and ROC, respectively. In FIG. 13, 0 is before LOC and 1 is after LOC. In FIG. 14, 0 is before ROC and 1 is after ROC. Table 7 shows the direction of change of each feature in each task.

TABLE 5

| Time on each side t (min) | Window length w (sec) | History h (sec) | AUC |
|---|---|---|---|
| 15 | 15 | 0 | 0.704 |
| 15 | 15 | 60 | 0.759 |
| 10 | 15 | 60 | 0.692 |
| 20 | 15 | 60 | 0.749 |

TABLE 5-continued

| Time on each side t (min) | Window length w (sec) | History h (sec) | AUC |
|---|---|---|---|
| 15 | 15 | 90 | 0.776 |
| 15 | 15 | 120 | 0.7993 |
| 15 | 30 | 120 | 0.797 |
| 15 | 10 | 60 | 0.753 |
| 15 | 10 | 120 | 0.7989 |

TABLE 6

| Time on each side t (min) | Window length w (sec) | History h (sec) | AUC |
|---|---|---|---|
| 10 | 15 | 0 | 0.701 |
| 15 | 15 | 0 | 0.726 |
| 15 | 15 | 60 | 0.750 |
| 10 | 15 | 60 | 0.803 |
| 20 | 15 | 60 | 0.755 |
| 15 | 15 | 120 | 0.744 |
| 15 | 30 | 120 | 0.733 |
| 15 | 10 | 60 | 0.755 |
| 15 | 10 | 120 | 0.745 |
| 10 | 15 | 120 | 0.744 |
| 10 | 10 | 120 | 0.751 |
| 10 | 30 | 120 | 0.720 |

According to Tables 5 and 6, the AUC for both tasks was approximately 0.8, indicating that the moment of LOC and ROC has discernible autonomic changes. Tables 5 and 6 indicate that 15 second windows are best for both tasks. However, for LOC, including more history (120 seconds) and a longer timeframe (+15 minutes) improves performance, while for ROC, less history (60 seconds) and a shorter overall timeframe (+10 minutes) is better.

In terms of subject-wise predictions, there is wide variability in how well even the best model performs across subjects. According to FIG. 13, LOC is aligned in time with autonomic changes for four subjects (02, 03, 07, 15), occurs before autonomic changes for one subject (05), and after autonomic changes for four subjects (04, 08, 09, 10). Treating the prediction as a probability of unconsciousness yields an interesting pattern across several of the subjects (including subjects 02, 03, 05, 07, 09, 10, and 15), where the probability spikes one or more times before finally rising up to a more stable higher value.

According to FIG. 14, ROC is aligned in time with autonomic changes for Subjects 03 and 07, occurs before autonomic changes for Subjects 05, 08, 09, 10, and 15, and after autonomic changes for Subjects 02 and 04. Finally, the progressive 'spiking' behavior of probability is not seen as clearly here compared to LOC.

Therefore, multimodal autonomic indices were used from around the time of LOC and ROC to test whether it is possible to differentiate pre-LOC (pre-ROC) from post-LOC (post-ROC), and if so, based on what autonomic dynamics. The results indicate that the time periods before and after both LOC and ROC can be differentiated with an AUC of around 0.8. A variety of total time lengths (t), window lengths (w), and durations of history (h) incorporated to identify the best set of hyperparameters for each task were tested.

In terms of hyperparameters the results indicate that 15-second windows are the adequate length to capture subtle autonomic changes while still having as much information as possible in each window. With respect to the fact that detection of LOC seems to benefit more from greater total time length and more history compared to ROC, this may be because there are more variable dynamics around ROC across subjects, so including more data makes generalization to a new subject more difficult.

The repeated 'spiking' pattern of the predicted probability of unconsciousness before LOC suggests that the autonomic dynamics are more complex than a smooth, linear transition between states. For ROC, behavioral changes (button pressing) seem to precede marked autonomic changes in most subjects. Any autonomic effects of the button pressing task are negligible compared to cardiovascular control changes and pharmacological intervention.

TABLE 7

|  | After v Before LOC | After v Before ROC |
| --- | --- | --- |
| muRR | + | + recent, -- before |
| sigmaRR | + | -- before, + recent |
| muHR |  | + |
| SigmaHR | + | + recent, -- before |
| Total Power | + recent, -- before | -- |
| LF | -- | + |
| HF | + | -- |
| LF/HF | + | -- |
| muPR | + | + |
| sigmaPR | + recent, -- before | -- |
| SBP | -- | + |
| DBP | + | -- |

A simpler version of Table 7 condensed by modality is below.

TABLE 8

| Covariate | After vs Before LOC | After vs Before ROC |
| --- | --- | --- |
| Heart rate variability | + | -- |
| Electrodermal Activity | + | + |
| Blood pressure | -- | + |

Finally, when examining the features which change at LOC and ROC (Table 7), the results in terms of HRV are mostly in line with what is known about propofol and anesthesia. For example, at LOC, there is an increase in the length and variability of the RR interval and parasympathetic tone (HF), a decrease in sympathetic tone (LF), and expected changes in BP. Similarly, for ROC, there are autonomic changes that align with expectation, such as an increase in heartrate, increase in sympathetic tone (LF), increase in EDA pulse rate, and increase in BP. However, in both cases, there are also dynamics that are unexpected or harder to interpret, such as the increase in electrodermal activity after LOC. This could be due to residual anxiety from before the study started or the burning feeling of propofol in one's veins. This could also be due to the other interventions such as phenylephrine, often given near LOC, which can change HRV dynamics.

These dynamics, as well as those seen with the subject-specific predictions, can only be appreciated because of the use of multimodal autonomic indices. HRV, EDA, and BP each capture different aspects of the autonomic nervous system, from central to peripheral and sympathetic to vagal. Including all of these modalities in models of anesthesia defines a more holistic physiologic state and elucidates subtler and not yet well understood interactions between the different modalities.

These result suggest that loss and regain of consciousness in general anesthesia are characterized by changing dynamics not only in the brain, but also in the autonomic nervous system. Further elucidation of these dynamics may help define a biomarker that is more objective than simple behavioral response tracking yet still robust and usable in low-resource settings without EEG. In addition, analyzing the interplay between different autonomic modalities during these transitions can shed light on the different roles they play in autonomic regulation.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that inventive embodiments may be practiced otherwise than as specifically described. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments disclosed herein may be implemented using hardware, software, or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of" shall have its ordinary meaning as used in the field of patent law.

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of administering an anesthetic agent to a sedated patient, the method comprising:
    measuring, with an electrodermal activity sensor, electrodermal activity of the sedated patient;
    measuring, with a heart rate sensor, heart rate variability of the sedated patient while measuring the electrodermal activity of the sedated patient;
    applying a point process model for electrodermal activity to the electrodermal activity of the sedated patient to yield electrodermal activity metrics;
    applying a point process model for heart rate variability to the heart rate variability of the sedated patient to yield heart rate variability metrics;
    combining the electrodermal activity metrics and the heart rate variability metrics into time windows of a specified length;
    processing each of the time windows in a statistical model to yield a probability that the sedated patient is perceiving nociception in that time window; and
    adjusting a dosage of the anesthetic agent administered to the sedated patient based on the probability that the sedated patient is perceiving nociception.

2. The method of claim 1, wherein measuring the heart rate variability comprises obtaining electrocardiography (ECG) data and/or pulse plethysmography data from the sedated patient, and further comprising:
    estimating the point process model for the heart rate variability based on the ECG data and/or the pulse plethysmography data.

3. The method of claim 2, wherein estimating the point process model for heart rate variability comprises:
    determining RR intervals between consecutive R wave peaks in the ECG data and/or the pulse plethysmography data, the RR intervals being time elapsed between the consecutive R wave peaks;
    determining at least one distribution of the RR intervals; and
    determining the heart rate variability from the at least one distribution of the RR intervals.

4. The method of claim 3, wherein determining the at least one distribution of the RR intervals comprises:
modeling the RR intervals using an inverse Gaussian model.

5. The method of claim 1, wherein the point process model for electrodermal activity is based on temporal information and/or amplitude information of the electrodermal activity.

6. The method of claim 1, wherein applying the point process model for electrodermal activity to the electrodermal activity of the sedated patient comprises:
extracting pulses from a phasic component of the electrodermal activity of the sedated patient.

7. The method of claim 6, wherein applying the point process model for electrodermal activity to the electrodermal activity of the sedated patient further comprises:
determining intervals between consecutive pulses in the electrodermal activity;
determining a distribution of the intervals; and
determining instantaneous estimates of a mean and a standard deviation of the intervals based on the distribution.

8. The method of claim 1, wherein, for each of the time windows, the electrodermal activity metrics comprise measures of pulses extracted from the electrodermal activity of the sedated patient and the heart rate variability metrics comprise mean heart rate, standard deviation of heart rate, and ratio of power in low frequency (LF) and high frequency (HF) ranges of the heart rate variability.

9. The method of claim 1, wherein the statistical model is a member of the group consisting of a neural network, a support vector machine, or a random forest.

10. The method of claim 1, further comprising, before applying the point process model for electrodermal activity to the electrodermal activity of the sedated patient:
identifying an artifact in the electrodermal activity of the sedated patient; and
correcting the artifact in the electrodermal activity of the sedated patient.

11. The method of claim 1, further comprising, before applying the point process model for electrodermal activity to the electrodermal activity of the sedated patient:
separating a tonic component from the electrodermal activity of the sedated patient.

12. The method of claim 1, wherein the point process model for electrodermal activity is based on temporal information of the electrodermal activity.

13. A method of administering an anesthetic agent to an unconscious patient, the method comprising:
measuring, with an electrodermal activity sensor, electrodermal activity of the unconscious patient;
measuring, with a heart rate sensor, heart rate variability of the unconscious patient while measuring the electrodermal activity of the unconscious patient;
identifying statistical structure in the electrodermal activity of the unconscious patient;
identifying statistical structure in the heart rate variability of the unconscious patient;
constructing at least one point process model of the electrodermal activity based on the statistical structure in the electrodermal activity of the unconscious patient;
constructing a point process model of the heart rate variability based on the statistical structure in the heart rate variability of the unconscious patient;
generating, with the at least one point process model of the electrodermal activity, a electrodermal activity vector representing instantaneous dynamics of the electrodermal activity of the unconscious patient;
generating, with the point process model of the heart rate variability, a heart rate variability vector representing instantaneous dynamics of the heart rate variability of the unconscious patient;
constructing a multimodal model based on the electrodermal activity vector and the heart rate variability vector;
estimating, with the multimodal model, a sympathetic-driven arousal state of the unconscious patient is perceiving nociception; and
adjusting a dosage of the anesthetic agent administered to the unconscious patient based on the sympathetic-driven arousal state.

14. The method of claim 13, wherein identifying the statistical structure in the electrodermal activity of the unconscious patient comprises:
separating the electrodermal activity of the unconscious patient into a tonic component and a pulsatile phasic component; and
extracting pulses from the pulsatile phasic component.

15. The method of claim 13, wherein constructing the at least one point process model of the electrodermal activity is based on statistical structure of temporal characteristics of the electrodermal activity of the unconscious patient.

16. The method of claim 13, wherein generating the electrodermal activity vector comprises determining amplitudes of pulses in the electrodermal activity for each of a plurality of time windows.

17. The method of claim 13, wherein generating the heart rate variability vector comprises determining instantaneous estimates of mean heart rate and standard deviation of heart rate for each of a plurality of time windows.

* * * * *